(12) United States Patent
Connell et al.

(10) Patent No.: US 6,200,971 B1
(45) Date of Patent: Mar. 13, 2001

(54) BICYCLIC HETEROCYCLIC COMPOUNDS

(75) Inventors: Richard Connell, Trumbull, CT (US); Siegfried Goldmann; Ulrich Müller, both of Wuppertal (DE); Stefan Lohmer, Milan (IT); Hilmar Bischoff; Dirk Denzer, both of Wuppertal (DE); Rudi Grü tzmann, Solingen (DE); Stefan Wohlfeil, Hilden (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/420,304

(22) Filed: Oct. 18, 1999

Related U.S. Application Data

(62) Division of application No. 09/099,557, filed on Jun. 18, 1998, now Pat. No. 6,025,378, which is a division of application No. 08/761,921, filed on Dec. 9, 1996, now Pat. No. 5,811,429.

(30) Foreign Application Priority Data

Dec. 15, 1995 (DE) .............................. 195 46 918

(51) Int. Cl.$^7$ ..................... A61K 31/54; A61K 31/535; A61P 9/10; C07D 279/16; C07D 265/36
(52) U.S. Cl. .................................... 514/224.2; 514/230.5; 514/300; 514/312; 544/48; 544/52; 544/105; 546/123; 546/155
(58) Field of Search ................ 514/224.2, 230.5, 514/300, 312; 544/48, 52, 105; 546/123, 155

(56) References Cited

U.S. PATENT DOCUMENTS 5,314,880 * 5/1994 Whittaker et al. ..................... 514/80

FOREIGN PATENT DOCUMENTS 0 513 533  * 11/1992 (EP) .
0 560 162  *  9/1993 (EP) .
0 560 163  *  9/1993 (EP) .
0 565 986  * 10/1993 (EP) .
0 610 698  *  8/1994 (EP) .

* cited by examiner

Primary Examiner—Mukund J. Shah
Assistant Examiner—Brenda Coleman
(74) Attorney, Agent, or Firm—Norris McLaughlin & Marcus

(57) ABSTRACT

The bicyclic heterocyclic compounds are prepared by reaction of correspondingly substituted carboxylic acids with amines, in particular with phenylglycinolamine. The bicyclic heterocyclic compounds according to the invention are suitable as active compounds in medicaments, in particular in medicaments having an antiatherosclerotic action.

5 Claims, No Drawings

BICYCLIC HETEROCYCLIC COMPOUNDS

This application is a divisional of application Ser. No. 09/099,557, filed on Jun. 18, 1998 (now U.S. Pat. No. 6,025,378); which is a divisional of application Ser. No. 08/761,921, filed on Dec. 9, 1996 (now U.S. Pat. No. 5,811,429).

The present invention relates to bicyclic heterocyclic compounds, processes for their preparation and their use in medicaments, in particular as antiatherosclerotic medicaments.

It is known that increased blood levels of triglycerides (hypertriglyceridaemia) and cholesterol (hypercholesterolaemia) are associated with the origin of atherosclerotic changes to the vascular wall and coronary heart disease.

Moreover, a significantly increased risk of developing coronary heart disease exists if these two risk factors occur in combination, which in turn is accompanied by excessive production of apolipoprotein B-100. There is therefore still a great need to provide active medicaments for combating atherosclerosis and coronary heart disease.

Benzimidazole derivatives having a PAF-antagonistic action furthermore are described in U.S. Pat. No. 5,314,880.

The present invention relates to bicyclic heterocyclic compounds of the general formula (I)

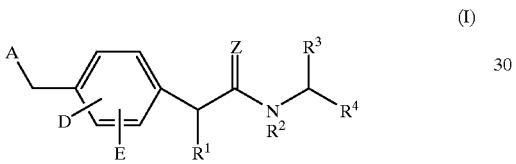

(I)

in which

A represents a radical of the formula

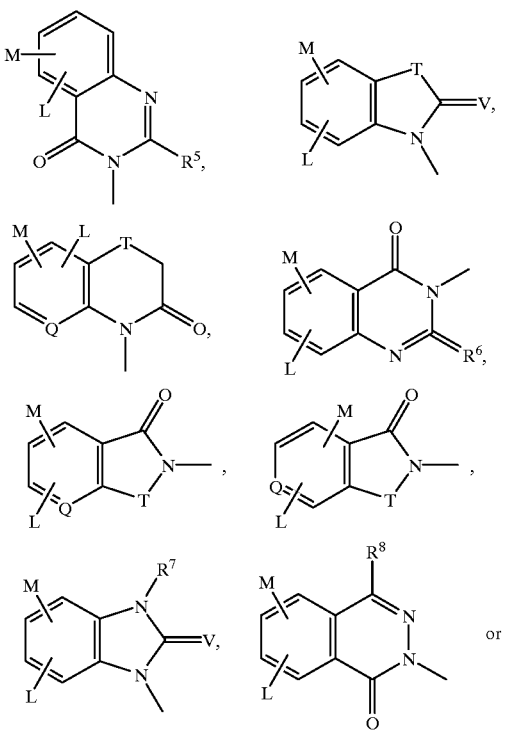

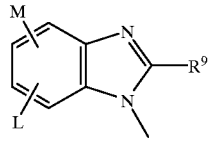

wherein

L and M are identical or different and denote hydrogen, halogen, trifluoromethyl, carboxyl, cycloalkyl having 3 to 6 carbon atoms, hydroxyl, phenyl, or straight-chain or branched alkyl, alkoxycarbonyl or alkoxy having in each case up to 6 carbon atoms, Q denotes a nitrogen atom or the —CH group, T denotes a group of the formula —SO$_2$ or —CO or an oxygen or sulphur atom, V denotes an oxygen or sulphur atom, $R^5$, $R^6$, $R^7$ and $R^8$ are identical or different and denote hydrogen, straight-chain or branched alkyl or branched alkyl having up to 6 carbon atoms, benzyl or phenyl, which are optionally substituted by halogen or by straight-chain or branched alkyl having up to 6 carbon atoms, $R^9$ denotes trifluoromethyl, benzyl or a 5- to 7-membered, optionally benzo-fused heterocyclic radical having up to 3 heteroatoms from the series consisting of S, N and/or O, which is optionally substituted up to 3 times in an identical or different manner by halogen, phenyl, hydroxyl or by straight-chain or branched alkyl or alkoxy having in each case up to 4 carbon atoms, or denotes a group of the formula —S(O)$_a$—$R^{10}$, wherein a denotes the number 0, 1 or 2, $R^{10}$ denotes straight-chain or branched alkyl or alkenyl having in each case up to 8 carbon atoms, which are optionally substituted by straight-chain or branched acyl having up to 6 carbon atoms or by aryl or aroyl having in each case up to 10 carbon atoms, which in turn can be substituted up to twice in an identical or different manner by halogen, trifluoromethyl or by straight-chain or branched acyl having up to 5 carbon atoms, or denotes aryl having 6 to 10 carbon atoms, which is optionally substituted by halogen, hydroxyl trifluoromethyl or straight-chain or branched alkyl or alkoxy having in each case up to 5 carbon atoms, D and E are identical or different and represent hydrogen, halogen, trifluoromethyl, hydroxyl or carboxyl, or represent straight-chain or branched alkyl, alkoxy or alkoxycarbonyl having in each case up to 6 carbon atoms, Z represents an oxygen or sulphur atom, $R^1$ represents cycloalkyl having 3 to 10 carbon atoms, or represents straight-chain or branched alkyl having 1 to 10 carbon atoms, or represents phenyl, which is optionally substituted up to twice in an identical or different manner by halogen, nitro, cyano, hydroxyl or straight-chain or branched alkyl or alkoxy having in each case up to 4 carbon atoms, $R^2$ represents hydrogen or straight-chain or branched alkyl having up to 3 carbon atoms, $R^3$ represents hydrogen or straight-chain or branched alkyl having up to 5 carbon atoms, or represents cycloalkyl having 3 to 7 carbon atoms, or represents phenyl or represents a 5- to 7-membered aromatic heterocyclic radical having up to 3 heteroatoms from the series consisting of S, N and/or O, which are optionally substituted up to 3 times in an identical or different manner by halogen, nitro, phenyl, hydroxyl or by straight-chain or branched alkyl or alkoxy having up to 6 carbon atoms, $R^4$ represents hydrogen, or represents a group of the formula —$CH_2$—OH or $CH_2O$—CO—$R^{11}$, wherein $R^{11}$ denotes hydrogen, straight-chain or branched alkyl having up to 8 carbon atoms or phenyl, which is optionally substituted up to 3 times in an identical or different manner by halogen, hydroxyl, cyano or straight-chain or branched alkyl or alkoxy having in each case up to 4 carbon atoms, and salts thereof.

The bicyclic heterocyclic compounds according to the invention can also be in the form of their salts. Salts with organic or inorganic bases or acids may be mentioned in general here.

Physiologically acceptable salts are preferred in the context of the present invention. Physiologically acceptable salts of the compounds according to the invention can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can likewise be metal or ammonium salts of the compounds according to the invention which have a free carboxyl group. Particularly preferred salts are, for example, sodium, potassium, magnesium or calcium salts, as well as ammonium salts which are derived from ammonia or organic amines, such as, for example, ethylamine, di- or triethylamine, di- or triethanolamine, dicyclohexylamine, dimethylaminoethanol, arginine, lysine, ethylenediamine or 2-phenylethylamine.

The compounds according to the invention can exist in stereoisomeric forms which either behave as mirror images (enantiomers) or do not behave as mirror images (diastereomers). The invention relates both to the enantiomers or diastereomers and to the particular mixtures thereof. These mixtures of the enantiomers and diastereomers can be separated into the stereoisomerically uniform constituents in a known manner.

In the context of the invention, a heterocyclic radical, which is optionally benzo-fused, in general represents a saturated or unsaturated 5- to 7-membered, preferably 5- or 6-membered, heterocyclic radical which can contain up to 3 heteroatoms from the series consisting of S, N and/or O and, in the case of a nitrogen atom, can also be bonded via this. Examples which may be mentioned are: indolyl, quinolyl, benzo[b]thienyl, benzo[b]furyl, pyridyl, thienyl, furyl, pyrrolyl, thiazolyl, oxazolyl, imidazolyl, morpholinyl or piperidyl. Quinolyl, furyl, pyridyl and thienyl are preferred.

Preferred compounds of the general formula (I) are those in which

A represents a radical of the formula

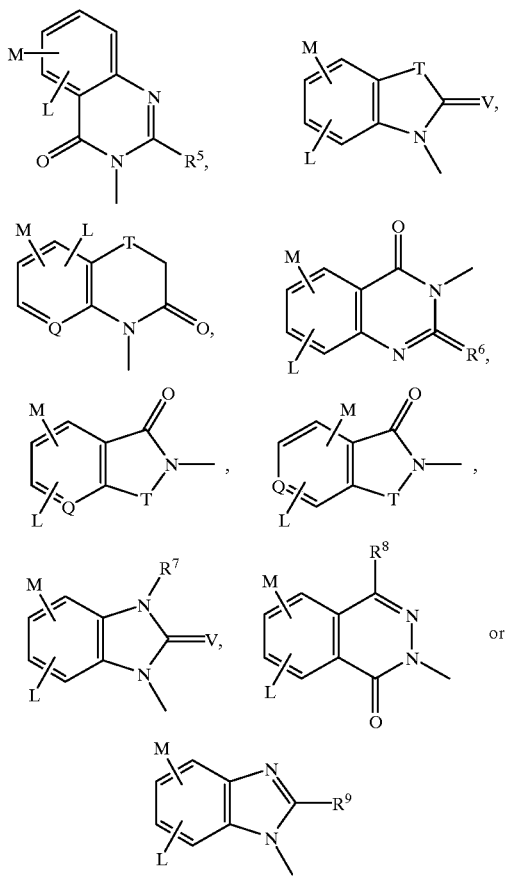

wherein

L and M are identical or different and denote hydrogen, fluorine, chlorine, bromine, trifluoromethyl, cyclopropyl, cyclobutyl, cyclopentyl, cyclohexyl, hydroxyl, phenyl or straight-chain or branched alkyl, alkoxycarbonyl or alkoxy having in each case up to 5 carbon atoms, Q denotes a nitrogen atom or the —CH group, T denotes a group of the formula —$SO_2$ or —CO or an oxygen or sulphur atom, V denotes an oxygen or sulphur atom, $R^5$, $R^6$, $R^7$ and $R^8$ are identical or different and denote hydrogen, straight-chain or branched alkyl having up to 5 carbon atoms, benzyl or phenyl, which are optionally substituted by fluorine, chlorine, bromine or by straight-chain or branched alkyl having up to 5 carbon atoms, $R^9$ denotes trifluoromethyl, benzyl, benzothienyl, thienyl, pyridyl, quinolyl, imidazolyl, furyl, pyrryl, oxazolyl or thiazolyl, which are optionally substituted up to 3 times in an identical or different manner by fluorine, chlorine, bromine, phenyl, hydroxyl or by straight-chain or branched alkyl or alkoxy having in each case up to 3 carbon atoms, or denotes a group of the formula —$S(O)_a$—$R^{10}$, wherein a denotes the number 0 or 1, $R^{10}$ denotes straight-chain or branched alkyl or alkenyl having in each case up to 6 carbon atoms, which are optionally substituted by straight-chain or branched acyl having up to 5 carbon atoms or by phenyl, benzoyl or naphthyl, which in turn can be substituted up to twice in an identical or different manner by fluorine, chlorine, bromine, trifluoromethyl or by straight-chain or branched acyl having up to 4 carbon atoms, or denotes naphthyl or phenyl, which are optionally substituted by fluorine, chlorine, bromine, hydroxyl, trifluoromethyl or straight-chain or branched alkyl or alkoxy having in each case up to 4 carbon atoms, D and E are identical or different and represent hydrogen, fluorine, chlorine, bromine, trifluoromethyl, hydroxyl or straight-chain or branched alkyl or alkoxy having in each case up to 4 carbon atoms, Z represents an oxygen or sulphur atom, $R^1$ represents cyclobutyl, cyclopentyl, cyclohexyl, cycloheptyl or cyclooctyl, or represents straight-chain or branched alkyl having up to 7 carbon atoms, or represents phenyl, which is optionally substituted by fluorine, chlorine, bromine, nitro, cyano, hydroxyl or straight-chain or branched alkyl or alkoxy having in each case up to 3 carbon atoms, $R^2$ denotes hydrogen or methyl, $R^3$ represents hydrogen or straight-chain or branched allyl having up to 4 carbon atoms, benzyl, cyclopropyl, cyclopentyl or cyclohexyl, or represents phenyl, pyridyl, thienyl or furyl which are optionally substituted up to twice in an identical or different manner by fluorine, chlorine, bromine, phenyl, nitro, hydroxyl or by straight-chain or branched alkyl or alkoxy having up to 4 carbon atoms, $R^4$ represents hydrogen, or represents a group of the formula —$CH_2$—OH or —$CH_2O$—CO—$R^{11}$, wherein
$R^{11}$ denotes hydrogen, straight-chain or branched alkyl having up to 6 carbon atoms or phenyl, which is optionally substituted up to twice in an identical or different manner by fluorine, chlorine, bromine, cyano, hydroxyl or straight-chain or branched alkyl or alkoxy having in each case up to 3 carbon atoms, and salts thereof Particularly preferred compounds of the general formula (I) are those in which A represents a radical of the formula

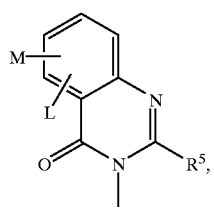
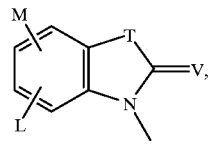
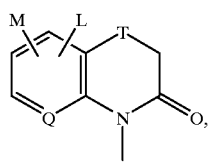
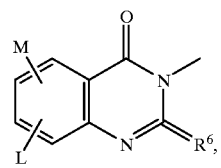
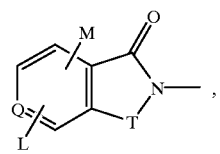
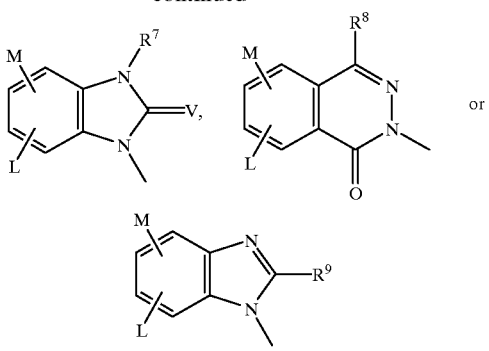

wherein
L and M are identical or different and denote hydrogen, fluorine, chlorine, bromine, hydroxyl, phenyl or straight-chain or branched alkyl or alkoxy having in each case up to 4 carbon atoms, Q denotes a nitrogen atom or the —CH group, T denotes a group of the formula —$SO_2$ or —CO or an oxygen or sulphur atom, V denotes an oxygen or sulphur atom, $R^5$, $R^6$, $R^7$ and $R^8$ are identical or different and denote hydrogen, straight-chain or branched allyl having up to 4 carbon atoms, benzyl or phenyl, which are optionally substituted by fluorine, chlorine, bromine or by straight-chain or branched alkyl having up to 4 carbon atoms, $R^9$ denotes trifluoromethyl benzyl, benzothienyl thienyl pyridyl, imidazolyl furyl or thiazolyl, which are optionally substituted up to 3 times in an identical or different manner by fluorine, chlorine, bromine, phenyl, hydroxyl or by straight-chain or branched alkyl or alkoxy having in each case up to 3 carbon atoms, or denotes a group of the formula —$S(O)_a$—$R^{10}$, wherein
a denotes the number 0 or 1,
$R^{10}$ denotes straight-chain or branched alkyl or alkenyl having in each case up to 5 carbon atoms, which are optionally substituted by straight-chain or branched acyl having up to 4 carbon atoms or by phenyl, benzoyl or naphthyl, which in turn can be substituted up to twice in an identical or different manner by fluorine, chlorine, bromine, trifluoromethyl or by straight-chain or branched acyl having up to 3 carbon atoms, or denotes naphthyl or phenyl, which are optionally substituted by fluorine, chlorine, bromine, hydroxyl, trifluoromethyl or straight-chain or branched alkyl or alkoxy having in each case up to 3 carbon atoms, D and E are identical or different and represent hydrogen, fluorine, chlorine, bromine or trifluoromethyl, Z represents oxygen, $R^1$ represents cyclopentyl, cyclohexyl, cycloheptyl or cyclooctyl, or represents straight-chain or branched alkyl having up to 6 carbon atoms, $R^2$ represents hydrogen or methyl, $R^3$ represents phenyl and $R^4$ represents the group —$CH_2$—OH, and salts thereof A process has furthermore been found for the preparation of the compounds of the general formula (I) according to the invention, characterized in that acids of the general formula (II)

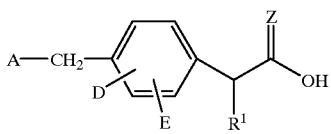

in which
A, D, E, Z and $R^1$ have the meaning given, are reacted with compounds of the general formula (III)

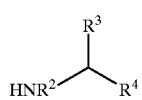

in which
$R^2$, $R^3$ and $R^4$ have the meaning given, in inert solvents and in the presence of bases and/or auxiliaries.

The process according to the invention can be illustrated by way of example by the following equation:

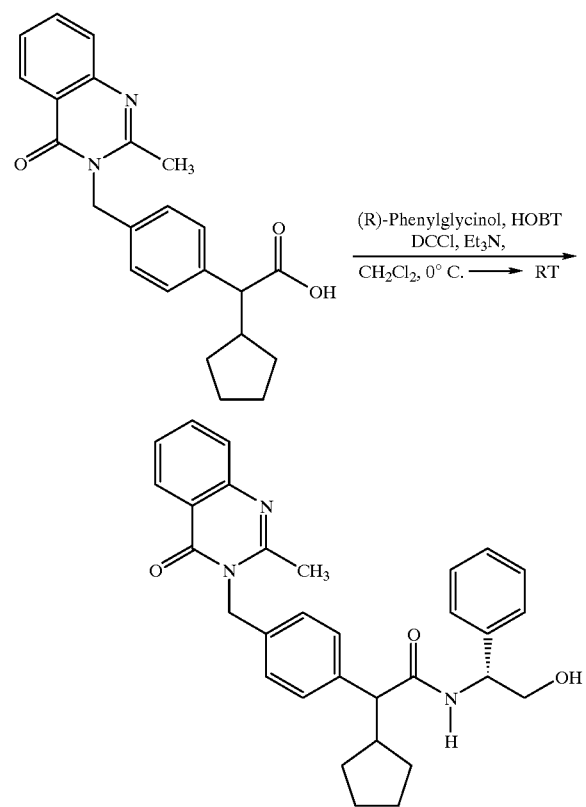

Suitable solvents here are inert organic solvents which do not change under the reaction conditions. These include ethers, such as diethyl ether or tetrahydrofuran, halogenated hydrocarbons, such as methylene chloride, chloroform, carbon tetrachloride, 1,2-dichloroethane, trichloroethane, tetrachloroethane, 1,2-dichloroethane or trichloroethylene, hydrocarbons, such as benzene, xylene, toluene, hexane, cyclohexane or petroleum fractions, nitromethane, dimethylformamide, acetone, acetonitrile or hexamethylphosphoric acid triamide. It is also possible to employ mixtures of the solvents. Methylene chloride, tetrahydrofuran, toluene or dimethylformamide are particularly preferred.

Inorganic or organic bases can in general be employed as bases for the process according to the invention. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or alkali metal or alkaline earth metal alcoholates, such as sodium or potassium methanolate, sodium or potassium ethanolate or potassium tert-butylate, or organic amines (trialkyl($C_1$–$C_6$)amines), such as triethylamine, or heterocyclic compounds, such as 1,4-diazabicyclo[2.2.2]octane (DABCO), 1,8-diazabicyclo[5.4.0]undec-7-ene (DBU), pyridine, diaminopyridine, methylpiperidine or morpholine. It is also possible to employ alkali metals, such as sodium, and hydrides thereof, such as sodium hydride, as bases. Sodium carbonate, potassium carbonate and triethylamine are preferred.

The base is employed in an amount of 1 mol to 5 mol preferably 1 mol to 3 mol, per mole of the compound of the general formula (II).

Dehydrating reagents are also suitable auxiliaries. These include, for example, carbodiimides, such as diisopropylcarbodiimide, dicyclohexylcarbodiimide or N-(3-dimethylaminopropyl)-N'-ethylcarbodiimide hydrochloride, or carbonyl compounds, such as carbonyldiimidazole, or 1,2-oxazolium compounds, such as 2-ethyl-5-phenyl-1,2-oxazolium 3-sulphonate, or propane-phosphoric anhydride or iso-butyl chloroformate or benzotriazolyloxy-tris-(dimethylamino)phosphonium hexafluorophosphate or phosphonic acid diphenyl ester-amide or methanesulphonyl chloride, if appropriate in the presence of bases, such as triethylamine or N-ethylmorpholine or N-methylpiperidine or dicyclohexyl-carbodiimide and N-hydroxysuccinimide.

The reaction is in general carried out in a temperature range from 0° C. to 150° C., preferably from +20° C. to +110° C.

The reaction can be carried out under normal increased or reduced pressure (for example 0.5 to 5 bar). It is in general carried out under normal pressure.

The compounds of the general formula (II) are new in most cases and can be prepared, for example, by a process in which compounds of the general formula (IV)

A—H  (IV)

in which
A has the meaning given, are reacted with compounds of the general formula (V)

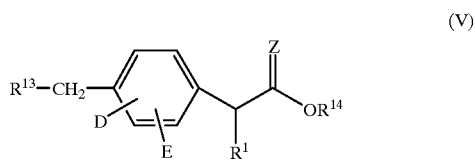

in which
D, E, Z and $R^1$ have the meaning given,
$R^{13}$ represents halogen, preferably chlorine or bromine, and $R^{14}$ represents straight-chain or branched alkyl having up to 6 carbon atoms, in inert solvents and in the presence of bases and/or auxiliaries, and, finally, the esters are hydrolysed by customary methods.

Customary organic solvents which do not change under the reaction conditions are suitable for the reaction. These include, preferably, ethers, such as diethyl ether, dioxane, tetrahydrofuran or glycol dimethyl ether, or hydrocarbons, such as benzene, toluene, xylene, hexane, cyclohexane or petroleum fractions, or halogenated hydrocarbons, such as methylene chloride, chloroform, carbon tetrachloride, dichloroethylene, trichloroethylene or chlorobenzene, or ethyl acetate, triethylamine, pyridine, dimethyl sulphoxide, dimethylformamide, hexamethylphosphoric acid triamide, acetonitrile, acetone or nitromethane. It is also possible to use mixtures of the solvents mentioned. Dimethylformamide, tetrahydrofuran and dimethyl sulphoxide are preferred.

Bases which can be employed are in general the abovementioned bases, but in particular the alkali metal hydrides, such as sodium hydride.

The base is in general employed in an amount of 0.05 mol to 10 mol, preferably 1 mol to 2 mol, per mole of the compound of the formula (IV).

The auxiliary is in general employed in an amount of 0.01 mol to 100 mol, preferably 0.1 mol to 10 mol, per mole of the compound of the general formula (IV).

The reaction is in general carried out in a temperature range from –30° C. to +100° C., preferably –10° C. to +60° C.

The reaction is in general carried out under normal pressure. However, it is also possible to carry out the processes under increased pressure or under reduced pressure (for example in a range from 0.5 to 5 bar).

The above mentioned dehydrating reagents are siutable auxiliaries.

The various amine/amide derivatives are also prepared using a large number of known methods, such as, for example, coupling of acid derivatives from peptide chemistry [in this context, cf. Bodanszky, The Practice of Peptide Synthesis: Springer Verlag Volume 21, 1984 and Organic Chemistry; Functional Group Transformations: Academic Press, Volume 12-1].

The ester hydrolysis is carried out by customary methods, by treating the esters with customary bases in inert solvents.

Suitable bases are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium carbonate or potassium carbonate or sodium bicarbonate. Sodium hydroxide or potassium hydroxide are particularly preferably employed.

Suitable solvents are water or the organic solvents customary for hydrolysis. These include, preferably, alcohols, such as methanol, ethanol, propanol, isopropanol or butanol, or ethers, such as tetrahydrofuran or dioxane, or dimethylformamide or dimethyl sulphoxide. Alcohols, such as methanol, ethanol, propanol or isopropanol, are particularly preferably used. It is also possible to employ mixtures of the solvents mentioned.

The ester hydrolysis is in general carried out in a temperature range from 0° C. to +100° C., preferably from +20° C. to +80° C.

The ester hydrolysis is in general carried out under normal pressure. However, it is also possible to carry out the hydrolysis under reduced pressure or under increased pressure (for example from 0.5 to 5 bar).

In carrying out the ester hydrolysis, the base is in general employed in an amount of 1 to 3 mol, preferably 1 to 1.5 mol, per mole of the ester. Molar amounts of the reactants are particularly preferably used.

The compounds of the general formula (III) are known per se.

The compounds of the general formula (I) according to the invention have a pharmacological action spectrum which cannot be foreseen.

They can be used as active compounds in medicaments for reducing changes to vascular walls and for treatment of coronary heart disease, cardiac insufficiency, disturbances in cerebral performance, ischaemic cerebral diseases, apoplexy, circulatory disturbances, disturbances in microcirculation and thromboses.

The proliferation of smooth muscle cells, furthermore, plays a decisive role in the occlusion of vessels. The compounds according to the invention suitable for inhibiting this proliferation and therefore for preventing atherosclerotic processes.

The compounds according to the invention are distinguished by a reduction in ApoB-100-associated lipoproteins (VLDL and its breakdown products, such as, for example, LDL), ApoB-100, triglycerides and cholesterol. They therefore have valuable pharmacological properties which are superior to the prior art.

Surprisingly, the action of the compounds according to the invention initially comprises a reduction in or complete inhibition of the formation and/or release of ApoB-100-associated lipoproteins from hepatic cells, which results in a lowering of the plasma VLDL level. This lowering in VLDL must be accompanied by a lowering of the plasma level of ApoB-100, LDL, triglycerides and cholesterol; several of the abovementioned risk factors which contribute to changes to the vascular wall are thus reduced simultaneously.

The compounds according to the invention can therefore be employed for prevention and treatment of atherosclerosis, obesity, pancreatitis and constipation.

1. Inhibition of the Release of ApoB-100-associated Lipoproteins

The test for detection of the inhibition of the release of ApoB-100-associated lipoproteins from hepatic cells was carried out in vitro with cultured hepatic cells, preferably with cells of the human line HepG2. These cells are cultured under standard conditions in medium for culture of eukaryotic cells, preferably in RPMI 1640 with 10% foetal calf serum. HepG2 cells synthesize and secrete into the culture supernatant ApoB-100-associated lipoprotein particles, which are in principle built up similarly to the VLDL and LDL particles which are to be found in plasma.

These particles can be detected with an immunoassay for human LDL. This immunoassay is carried out with antibodies which have been induced against human LDL in rabbits under standard conditions. The anti-LDL antibodies (rab-anti-LDL-Ab) were purified by affinity chromatography on an immunosorbent with human LDL. These purified rab-anti-LDL-Ab are adsorbed onto the surface of plastic. This adsorption is expediently carried out on the plastic surface of microtiter plates with 96 wells, preferably on MaxiSorp plates. If ApoB-100-associated particles are present in the supernatant of Hep-G2 cells, these can bond to the insolubilized rab-anti-LDL-Ab, and an immune complex bonded to the plastic surface is formed. Non-bonded proteins are removed by washing. The immune complex on the plastic surface is detected with monoclonal antibodies, which have been induced against human LDL and purified under standard conditions. These antibodies were conjugated with the enzyme peroxidase. Peroxidase converts the colourless substrate TMB into a coloured product in the presence of $H_2O_2$. After acidification of the reaction mixture with $H_2SO_4$, the specific absorption of light is determined at 450 nm, this being a measure of the amount of ApoB-100-associated particles which had been secreted by the HepG2 cells into the culture supernatant.

Surprisingly, the compounds according to the invention inhibit the release of ApoB-100-associated particles. The $IC_{50}$ value indicates the concentration of substance at which the absorption of light is inhibited by 50% compared with the control (solvent control without the substance).

| Example No. | Apo B $IC_{50}$ [nM] |
| --- | --- |
| 1 | 44.4 |
| 2 | 38.1 |
| 3 | 11.6 |
| 4 | 298.5 |
| 5 | 36.0 |
| 6 | 8.0 |
| 7 | 150.3 |
| 8 | 4.7 |
| 9 | 2.8 |
| 10 | 9.5 |
| 11 | 4.7 |
| 12 | 12.6 |
| 13 | 14.3 |
| 14 | 130.2 |
| 18 | 930.2 |
| 19 | 387.6 |
| 20 | 248.3 |
| 23 | 147.1 |
| 24 | 16.3 |
| 25 | 7.3 |
| 26 | 4.5 |
| 27 | 90.9 |
| 28 | 27.9 |
| 29 | 9.3 |
| 30 | 111.7 |
| 31 | 7.3 |
| 32 | 5.3 |
| 33 | 5.3 |
| 34 | 26.6 |
| 35 | 11.2 |
| 36 | 9.1 |
| 37 | 3.6 |
| 38 | 36.3 |
| 39 | 81.7 |
| 40 | 69.0 |
| 41 | 10.6 |
| 42 | 11.2 |
| 43 | 5.3 |
| 44 | 11.3 |
| 47 | 18.8 |
| 48 | 6.3 |
| 49 | 3.6 |
| 50 | 17.9 |
| 51 | 5.7 |
| 52 | 517.9 |
| 53 | 1694.9 |
| 54 | 60.2 |
| 55 | 19.5 |
| 57 | 5.0 |
| 58 | 251.0 |
| 59 | 29.2 |
| 60 | 9.7 |
| 61 | 38.9 |
| 62 | 122.9 |
| 63 | 5.9 |
| 67 | 27.4 |
| 68 | 70.6 |
| 70 | 58.3 |
| 71 | 29. |
| 72 | 392.9 |
| 73 | 29.4 |
| 76 | 37.2 |
| 77 | 14.9 |
| 78 | 279.3 |
| 79 | 15.2 |
| 80 | 7.5 |
| 81 | 8.5 |

2. Determination of VLDL Secretion in vivo on the Hamster

The Effect of the test substances on VLDL secretion in vivo is investigated on the hamster. For this, after premedication with atropine (83 mg/kg s.c.), golden hamsters are anaesthetized with Ketavet (83 mg/kg s.c.) and Nembutal (50 mg/kg i.p.). When the animals have become reflex-free, the v. jugularis is exposed and cannulated. 0.25 ml/kg of a 20% strength solution of Triton WR-1339 in physiological saline solution is then administered. This detergent inhibits lipoprotein lipase and thus leads to an increase in the triglyceride level because of an absence of catabolism of secreted VLDL particles. This increase in triglycerides can be used as a measure for the rate of VLDL secretion. Blood was taken from the animals by puncture, of the retroorbital venous plexus before one and two hours after administration of the detergent. The blood is incubated at room temperature for 2 hours and then at 4° C. overnight in order to conclude coagulation completely. Thereafter, it is centrifuged at 10,000 g for 5 minutes. The triglyceride concentration in the serum thus obtained is determined with the aid of a modified commercially obtainable enzyme test (Merckotest® Triglyceride No. 14354). 100 µl of test reagent are added to 100 µl of serum in 96-well plates and the plates are incubated at room temperature for 10 minutes. The optical density is then determined at a wavelength of 492 nm in an automatic plate reader (SLT-Spectra). Serum samples having a triglyceride concentration which is too high are diluted with physiological saline solution. The triglyceride concentration contained in the samples is determined with the aid of a standard curve measured in parallel. In this model, test substances are administered either intravenously immediately before administration of the detergent or orally or subcutaneously before initiation of the anaesthesia.

3. Inhibition of Intestinal Triglyceride Absorption in vivo (Rats)

The substances which are to be investigated in vivo for their inhibiting action on triglyceride absorption are administered orally to male Wistar rats having a body weight of between 170 and 230 g. For this purpose, the animals are divided into groups of 6 animals 18 hours before administration of the substance, and their food is then withdrawn. Drinking water is available to the animals ad libitum. The animals of the control groups are given an aqueous tragacanth suspension or a tragacanth suspension which comprises olive oil. The tragacanth-olive oil suspension is prepared with an Ultra-Turrax. The substances to be investigated are suspended in a corresponding tragacanth-olive oil suspension, likewise with an Ultra-Turrax, directly before administration of the substance.

Before administration by a stomach tube, blood is taken from each rat by puncture of the retroorbital venous plexus for determination of the basal serum triglyceride content. The tragacanth suspension, the tragacanth-olive oil suspensions without a substance (control animals) or the substances, suspended in a corresponding traganth-olive oil suspension, are then administered to the fasting animals using a stomach tube. Further blood for determination of the postprandial serum triglyceride increase is as a rule taken 1, 2 and 3 hours after the administration by stomach tube.

The blood samples are centrifuged and, after isolation of the serum, the triglycerides are determined photometrically with an EPOS-Analyzer 5060 (Eppendorf Gerätebau, Netheler & Hinz GmbH, Hamburg). The triglycerides are determined completely enzymatically with a commercially available UV test.

The postprandial increase in serum triglycerides is determined by subtraction of the triglyceride prevalue of each animal from its corresponding postprandial triglyceride concentrations (1, 2 and 3 hours after administration).

The average is taken of the differences (in mmol/l) at each point in time (1, 2 and 3 hours) in the groups, and the means of the increase in serum triglycerides (ΔTG) of the animals treated with the substance are compared with the animals which received only the tragacanth-oil suspension.

The chronological change in serum triglyceride in the control animals, which were given only tragacanth, is also calculated. The effect of the substance at each point in time (1, 2 or 3 hours) is determined as follows and stated in Δ% of the oil-loaded control.

$$\Delta\% \text{ increase in triglyceride} = \frac{\Delta TG_{substance} - \Delta TG_{tragacanth\ control}}{\Delta TG_{oil\ loading} - \Delta TG_{tragacanth\ control}} \times 100$$

Effect of 10 mg of test substance/kg of body weight p.o. on the increase in triglycerides (Δ%) 2 hours after a triglyceride loading in the serum of fasting rats. The increase in serum triglycerides of fat-loaded control animals based on the serum triglyceride level of tragacanth control animals, corresponds to 100%. n=6 animals per group.

The statistical analysis is carried out with the Student t-test after first checking the variances for homogeneity.

Substances which statistically significantly (p<0.05) reduce the postprandial increase in serum triglyceride by at least 30%, compared with the untreated control group, at a point in time are regarded as pharmacologically active.

| Example No. | Inhibition of intestinal absorption of triglycerides in vivo (rats) |
| --- | --- |
| 3 | 2 mg/kg |
| 5 | 2–3 mg/kg |
| 6 | <3 mg/kg |
| 8 | >6 mg/kg |
| 9 | 2–4 mg/kg |
| 10 | 3 mg/kg |
| 21 | >6 mg/kg |
| 22 | 7 mg/kg |
| 26 | 10 mg/kg |
| 29 | >/=3 mg/kg |
| 30 | >>10 mg/kg |
| 32 | 3–6 mg/kg |
| 33 | 2 mg/kg |
| 34 | >6 mg/kg |
| 38 | >2 mg/kg |
| 39 | 2 mg/kg |
| 40 | >>6 mg/kg |
| 41 | >>2 mg/kg |
| 44 | >2 mg,kg |
| 45 | 3 mg/kg |
| 46 | >>2 mg/kg |
| 48 | 3 mg/kg |
| 51 | >>10 mg/kg |
| 52 | 3 mg/kg |
| 54 | 6 mg/kg |
| 57 | 2 mg/kg |
| 60 | 6 mg/kg |
| 64 | >>10 mg/kg |
| 68 | >10 mg/kg |
| 70 | >>2 mg/kg |
| 74 | >>2 mg/kg |
| 77 | 8 mg/kg |

4. Inhibition of VLDL Secretion in vivo (Rats)

The action of the test substances on VLDL secretion is also investigated on the rat. For this, 500 mg/kg body weight (2.5 mg/kg) of Triton WR-1339, dissolved in physiological saline solution, is administered intravenously into the tail vein of rats. Triton WR-1339 inhibits lipoprotein lipase and thus leads to an increase in the triglyceride and cholesterol level due to inhibition of VLDL catabolism. These increases can be used as a measure of the rate of VLDL secretion.

Blood is taken from the animals by puncture of the retroorbital venous plexus before and one and two hours after administration of the detergent. The blood is incubated at room temperature for 1 hours, for coagulation, and the serum is isolated by centrifugation at 10,000 g for 20 seconds. The triglycerides are then determined photometrically at a wavelength of 540 nm by means of a commercially available coupled enzyme test (Sigma Diagnostics®, No. 339). Measurement is carried out with the aid of a similarly coupled enzyme test (Boehringer Mannheim®, No. 1442350) at a wavelength of 546 nm. Samples with triglyceride or cholesterol concentrations which exceed the measurement range of the methods are diluted with physiological saline solution. The particular serum concentrations are determined with the aid of standard series measured in parallel. Test substances are administered orally, intravenously or subcutaneously immediately after the Triton injection.

The invention furthermore relates to the combination of bicyclic heterocyclic compounds of the general formula (I) with a glucosidase and/or amylase inhibitor for treatment of familial hyperlipidaemias, obesity (adiposity) and diabetes mellitus. Glucosidase and/or amylase inhibitors in the context of the invention are, for example, acarbose, adiposine, voglibose (AO-128), miglitol, emiglitate, MDL-25637, camiglibase (MDL-73945), temdamistate, AI-3688, trestatin, pradimicin-Q and salbostatin. The combination of acarbose, miglitol, emiglitate or vaglibose with one of the abovementioned compounds of the general formula (I) according to the invention is preferred.

The new active compounds can be converted in a known manner into the customary formulations, such as plain tablets, coated tablets, pills, granules, aerosols, syrups, emulsions, suspensions and solutions, using inert, non-toxic, pharmaceutically suitable excipients or solvents. The therapeutically active compound should be present here in each case in a concentration of about 0.5 to 90% by weight of the total mixture, i.e. in amounts which are sufficient to achieve the stated dosage range.

The formulations are prepared, for example, by extending the active compounds with solvents and/or excipients, if appropriate using emulsifying agents and/or dispersing agents, it being possible, for example if water is used as the diluent, to use organic solvents as auxiliary solvents if appropriate.

The formulations are administered in the customary manner, preferably orally or parenterally, in particular perlingually or intravenously.

In the case of parenteral use, solutions of the active compound can be employed, using suitable liquid carrier materials.

In general, it has proved advantageous in the case of intravenous administration to administer amounts of about 0.001 to 1 mg/kg, preferably about 0.01 to 0.5 mg/kg of body weight to achieve effective results, and in the case of oral administration the dosage is about 0.01 to 20 mg/kg preferably 0.1 to 10 mg/kg of body weight.

Nevertheless, it may be necessary to deviate from the amounts mentioned, and in particular as a function of the body weight or the nature of the administration route, of the behaviour of the individual towards the medicament, the nature of the formulation thereof and the time or interval at which administration takes place. Thus, in some cases it may be sufficient to manage with less than the abovementioned minimum amount, while in other cases the upper limit mentioned must be exceeded. In the case where relatively large amounts are administered, it may be advisable to divide these into several individual doses over the course of the day.

Abbreviations used:

| | |
|---|---|
| CI | Chemical Ionization |
| cHept | Cycloheptyl |
| cHex | Cyclohexyl |
| cPent | Cyclopentyl |
| d | Doublet |
| DCCI | N'-(3-Dimethylaminopropyl)-N'-ethylcarbodiimide |
| dd | Doublet doublets |
| dia | Diastereomer |
| DMF | N,N-Dimethylformamide |
| DMSO | Dimethyl sulphoxide |
| EI | Electron impact ionization |
| FAB | Fast Atom Bombardment |
| HOBT | 1-Hydroxy-1H-benzotriazole |
| Hz | Hertz |
| iBu | Isobutyl |
| iPr | Isopropyl |
| m | Multiplet |
| Me | Methyl |
| nPr | Normal propyl |
| Ph | Phenyl |
| RT | Room temperature |
| s | Singlet |
| t | Triplet |
| TFA | Trifluoroacetic acid |
| THF | Tetrahydrofuran |
| TMS | Tetramethysilane |

Solvent mixtures used

| | | |
|---|---|---|
| Petroleum ether:acetone | 1:1 | (A) |
| Petroleum ether:ethyl acetate | 20:1 | (B) |
| Petroleum ether:ethyl acetate | 10:1 | (C) |
| Petroleum ether:ethyl acetate | 5:1 | (D) |
| Petroleum ether:ethyl acetate | 3:1 | (E) |
| Petroleum ether:ethyl acetate | 4:1 | (F) |
| Petroleum ether:ethyl acetate | 2:1 | (G) |
| Petroleum ether:ethyl acetate | 1:1 | (H) |
| Petroleum ether:ethyl acetate | 1:2 | (I) |
| Methylene chloride:methanol | 50:1 | (J) |
| Methylene chloride:methanol | 20:1 | (K) |
| Methylene chloride:methanol | 10:1 | (L) |
| Methylene chloride:ethyl acetate | 1:1 | (M) |
| Methylene chloride:ethanol | 50:1 | (N) |
| Methylene chloride (100%) | | (O) |
| Ethyl acetate:methanol | 10:1 | (P) |
| Toluene (100%) | | (Q) |
| Toluene:ethyl acetate | 1:1 | (R) |
| Toluene:ethyl acetate | 8:1 | (S) |
| Toluene:ethyl acetate | 9:1 | (T) |
| Cyclohexanol:ethyl acetate | 1:1 | (U) |
| Cyclohexanol:ethyl acetate | 7:3 | (V) |

Additional Information

If FAB has not been used, the following identifications apply in all the Tables which follow:

*=EI
=CI (NH$_3$)

EXAMPLE I

Methyl 2-(R&S)-phenyl-2-(4-methyl)phenylacetate

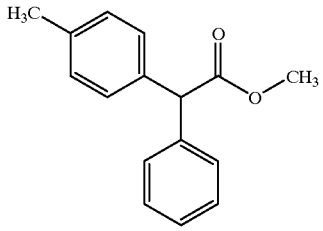

21.0 g (100 mmol, apin) of 2-phenyl-1-(4-methyl)phenyl-1-oxoethane and 38.8 g (120 mmol) of iodobenzenediacetate were dissolved in 300 ml of trimethyl orthoformate. 19.6 g of concentrated sulphuric acid were added to this solution and the solution was heated at 60° C. for 6 hours. It was cooled to room temperature, diluted with water (100 ml) and extracted with diethyl ether. The combined organic phases were dried over sodium sulphate and concentrated on a rotary evaporator. The residue was purified by column chromatography.

Yield 13.1 g(55%);

$R_f$=0.33 (petroleum ether:ethyl acetate, 20:1);

Mass (calculated) for $C_{16}H_{16}O_2$=240.30; mass spectrum (FAB, relative intensity) 241 (25%), 181 (100%);

$^1$H NMR (200 MHz, CDCl$_3$) δ7.3–7.10 (m, 9 H), 4.99 (s, 1 H), 3.73 (s, 3 H), 2.31 (2, 3 H).

EXAMPLE II tert-Butyl 2-cyclopentyl-2-(4-methylphenyl)-acetate

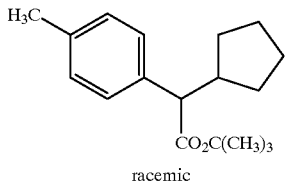

racemic 33.5 g (0.3 mol) of potassium tert-butylate are initially introduced into 100 ml of anhydrous DMF at 0° C., and 51.6 g (0.25 mol) of tert-butyl 4-methylphenyl-acetate in 250 ml of anhydrous DMF are added dropwise. The mixture is stirred at 0° C. for 30 minutes, 32.2 ml (0.3 mol) of cyclopentyl bromide in 150 ml of anhydrous DMF are added dropwise at 5–15° C. and the mixture is stirred at 25° C. for 20 hours. After concentration, the residue is partitioned between water and diethyl ether and the ether phase is dried over sodium sulphate and concentrated. The product crystallizes out.

Yield: 67 g (97.5% of theory);

Melting point: 51–53° C.

The compounds of Table I are prepared analogously to the instructions, of Example II:

TABLE I

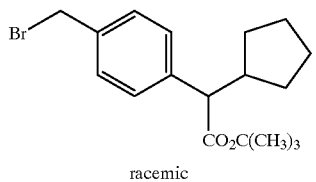

| Example No. | $R^1$ | $R^{18}$ | $R_f$* |
|---|---|---|---|
| III | (R & S) iPr | Me | 0.86 (T) |
| IV | (R & S) iBu | tBu | 0.84 (S) |
| V | (R & S) cPent | Me | 0.59 (C) |
| VI | (R & S) cHex | Me | 0.38 (B) |
| VII | (R & S) cHex | tBu | 0.71 (Q) |
| VIII | (R & S) cHept | Me | 0.57 (Q) |
| IX | (R & S) cHept | tBu | 0.32 (Q) |

EXAMPLE X tert-Butyl 2-(4-bromomethyl-phenyl)-2-cyclopentyl-acetate racemic 27.4 g (0.1 mol) of the compound from Example II are dissolved in 200 ml of carbon tetrachloride and the solution is heated to the boiling point. After addition of 0.82 g of azobisisobutyronitrile, 18.7 g (0.105 mol) of N-bromosuccinimide are added in portions, the mixture is then refluxed for 1 hour and cooled to 0° C. and the succinimide is filtered off. After concentration of the filtrate, the product precipitates out. It is washed with petroleum ether (40/60) and dried.

Yield: 20 g (57% of theory);

Melting point: 73–76° C.

The compounds of Table II are prepared analogously to the instructions of Example X:

TABLE II

| Example No. | $R^1$ | $R^{19}$ | $R_f$* | | Starting compound |
|---|---|---|---|---|---|
| XI | (R & S) iPr | Me | 0.78 | (O) | III |
| XII | (R & S) iBu | tBu | 0.86 | (O) | IV |
| XIII | (R & S) cPent | Me | 0.63 | (C) | V |
| XIV | (R & S) cHex | Me | 0.74 | (O) | VI |
| XV | (R & S) cHex | tBu | 0.58 | (C) | VII |
| XVI | (R & S) cHept | tBu | 0.84 | (O) | VIII |
| XVII | (R & S) Ph | Me | 0.74 | (O) | IX |

EXAMPLE XVIII

4-Carboethoxy-2-phenylthiazole

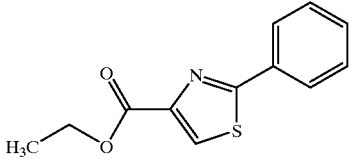

13.19 g (96 mmol) of thiobenzamide are dissolved in 260 ml of THF. A solution of 25.0 g (115.37 mmol, 90% pure) of ethyl bromopiruvate in 250 ml of THF is added dropwise at room temperature. During this operation, the temperature rises to 35° C. The mixture is boiled under reflux overnight and concentrated on a rotary evaporator and the residue is extracted with ethyl acetate and saturated $NaHCO_3$ solution. The organic phase is dried over sodium sulphate and concentrated on a rotary evaporator. The residue is purified by column chromatography (silica gel Merck 60 (0.040–0.063)):

Yield: 20.1 g (89.6%);

$R_f$=0.66 (petroleum ether:ethyl acetate 3:1);

Mass (calculated) for $C_{12}H_{11}NO_2$=233.29; mass spectrum (CI, relative intensity) 234 (100%);

$^1$H NMR (200 MHz, $CDCl_3$) δ8.15 (s, 1 H), 8.03–7.99 (m, 2 H), 7.48–7.42 (m, 3 H), 4.46 (q, J=7.11 Hz, 2 H), 1.43 (t, J=7.16 Hz, 3 H).

EXAMPLE XIX

4-Carboxy-2-phenylthiazole

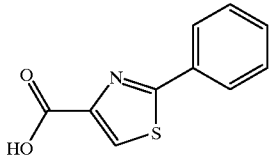

20.1 g (86.2 mmol) of the compound from Example XVII are dissolved in 400 ml of ethanol. A solution of 17.2 g (430.8 mmol) of sodium hydroxide lozenges in 80 ml of water is added. The mixture is boiled under reflux for 6 hours. Water is added and the pH is brought to 6 with half-concentrated hydrochloric acid, while cooling with ice. The mixture is concentrated on a rotary evaporator and the residue is extracted with ethyl acetate and water. The organic phase is dried over sodium sulphate and concentrated on a rotary evaporator.

Yield: 13.6 g (76.9%);

Melting point=170–172° C.;

$R_f$=0.11 ($CH_2Cl_2$:methanol, 20:1);

Mass (calculated) for $C_{10}H_7NO_2S$=205.24; mass spectrum (EI, relative intensity) 205 (100%);

$^1$H NMR (250 MHz, DMSO-$D_6$) δ13.2 (bs, 1 H), 8.52 (s, 1 H), 8.01–7.96 (m, 2 H), 7.60–7.45 (m, 3 H).

EXAMPLE XX

2-[4-(2-Phenyl)thiazolyl]benzimidazole

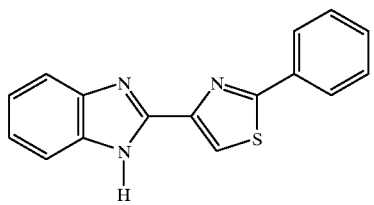

13.3 g (64.8 mmol) of the compound from Example XIX and 7.0 g (64.8 mmol) of diaminobenzene are mixed with one another. 70 ml of polyphosphoric acid are slowly added, while stirring constantly with an overhead stirrer. The mixture is heated at 100° C. for 1 hour and at 140° C. for 6 hours. Water and sodium hydroxide lozenges are added, while cooling with ice, and the pH is brought to 12. Ethyl acetate is added and the mixture is extracted. The organic phase is dried over sodium sulphate and concentrated on a rotary evaporator. The residue is triturated with $CH_2Cl_2$, filtered off with suction and dried.

Yield: 4.3 g (23.9%);

Melting point=183–191° C.;

$R_f$=0.51 (petroleum ether:ethyl acetate, 1:1);

Mass (calculated) for $C_{16}H_{11}N_3S$=277.35; mass spectrum (EI, relative intensity) 277 (85%), 174 (100%);

$^1$H NMR (250 MHz, DMSO-$D_6$) δ12.9 (bs, 1 H), 8.44 (s, 1 H), 8.16–8.09 (m, 2 H), 7.63–7.52 (m, 5 H), 7.27–7.22 (2 H).

The compounds listed in Table III were prepared analogously to the instructions of Example XX:

TABLE III

| Example No. | A | Yield (% of theory) | $R_f$ (solvent) | Melting point (° C.) | MS (EI) (relative intensity) |
|---|---|---|---|---|---|
| XXI | 5,6-dichloro-1-methyl-2-CH₂Ph-benzimidazole | 23 | 0.52 (K) | 184–86 | 278 (60%), 277 (55%), 276 (100%), 175 (95%) |
| XXII | 1-methyl-2-(benzothiophen-2-yl)benzimidazole | 22 | 0.72 (R) | 216–24 | 250 (100%) |
| XXIII | 1-methyl-2-(thiophen-3-yl)benzimidazole | 23 | 0.80 (P) | 165 | 200 (20%), 111 (100%) |
| XXIV | 1-methyl-2-(pyridin-4-yl)benzimidazole | 60 | 0.47 (P) | 204–10 | 195 (100%) |
| XXV | 1-methyl-2-(pyridin-3-yl)benzimidazole | 36 | 0.39 (P) | >240 | 195 (100%) |
| XXVI | 1-methyl-2-CH₂Ph-benzimidazole | 33 | 0.40 (P) | 182–84 | 208 (95%), 207 (100%) |

TABLE III-continued

| Example No. | A | Yield (% of theory) | $R_f$ (solvent) | Melting point (° C.) | MS (EI) (relative intensity) |
|---|---|---|---|---|---|
| XXVII | 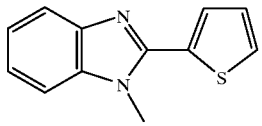 | 19 | 0.45 (P) | >220 | 200 (100%) |

EXAMPLE XXVIII tert-butyl 2-cyclopentyl-2-[4-(2-methyl-4-oxo-4H-quinazolin-3-yl-methyl)phenyl]acetate

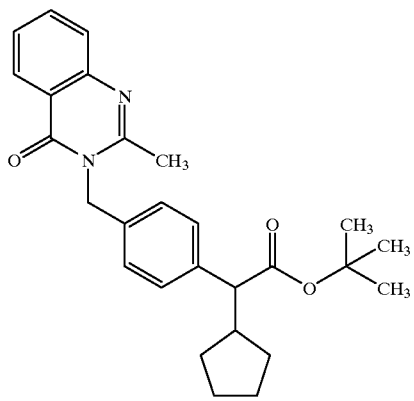

374 mg (9.34 mmol) of sodium hydride (60% pure in paraffin) are initially introduced into 1.0 ml of DMF. The mixture is cooled to 0° C. and a solution of 1.50 g (9.34 mmol) of 2-methyl-4(3H)-quinazolinone in 15 ml of DMF is slowly added dropwise. The mixture is subsequently stirred for half an hour, during which the temperature rises to 20° C. The mixture is cooled again, 3.0 g (8.49 mmol) of the compound from Example II are dissolved in 20 ml of DMF, and this solution is added dropwise. The mixture is stirred overnight at room temperature. Water is poured in and the mixture is extracted (3 times) with ether. The combined organic phases are dried over sodium sulphate and concentrated on a rotary evaporator. The residue is purified by column chromatography (silica gel Merck 60 (0.040–0.063)):

Yield: 2.88 g (78.3%);

Melting point=128° C.;

$R_f$=0.54 ($CH_2Cl_2$:methanol, 100:5);

Mass (calculated) for $C_{27}H_{32}N_2O_3$=432.567; mass spectrum (FAB, relative intensity) 433 (100%), 377 (100%), 376 (40%);

$^1$H NMR (250 MHz, $CDCl_3$) δ8.31 (dd, J=7.59 Hz, J=1.25 Hz, 1 H), 7.77 (m, 1 H), 7.63 (d, J=8.0 Hz, 1 H), 7.47 (m, 1 H), 7.28 (d, J=8.22 Hz, 2 H), 7.14 (d, J=8.26 Hz, 2 H), 5.37 (s, 2 H), 3.12 (d, J=11.06 Hz, 1 H), 2.54 (s, 3 H), 2.47 (m, 1 H), 1.90 (m, 1 H), 1.65–1.10 (m, 6 H), 1.38 (s, 9 H), 0.92 (m, 1 H);

$^{13}$C NMR (50 MHz, $CDCl_3$) δ173.02 (s), 162.41 (s), 154.63 (s), 147.36 (s), 139.16 (s), 134.40 (d), 134.37 (s), 128.74 (d), 127.12 (d), 126.72 (d), 126.59 (d), 126.51 (d), 120.39 (s), 80.55 (s), 58.60 (d), 46.89 (t), 43.67 (d), 31.24 (t), 30.77 (t), 27.96 (q), 25.13 (t), 24.82 (t), 23.48 (q).

The compounds listed in Table IV are prepared analogously to the instructions of Example XXVIII:

TABLE IV

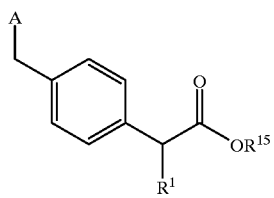

| Table No. | A | $R^1$ | $R^{15}$ | Yield (% of theory) | $R_f$ (solvent) | Melting point (°C.) | MS (relative intensity) |
|---|---|---|---|---|---|---|---|
| XXIX | 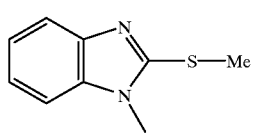 | (R & S) cPent | Me | 100 | 0.33 (J) | | 395 (100%) |

TABLE IV-continued

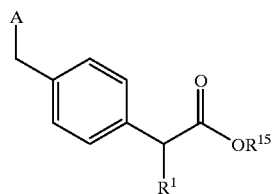

| Table No. | A | R¹ | R¹⁵ | Yield (% of theory) | R_f (solvent) | Melting point (°C.) | MS (relative intensity) |
| --- | --- | --- | --- | --- | --- | --- | --- |
| XXX | 1-methyl-2-(methylthio)benzimidazol-5-yl | (R & S) cHept | tBu | 78 | 0.32 (J) | 101 | *464 (100%) |
| XXXI | 1,5,6-trimethyl-2-(methylthio)benzimidazol-... | (R & S) cPent | Me | 28 | 0.54 (J) 0.33 (E) | 121 | 423 (100%) |
| XXXII | 1-methyl-2-(ethylthio)benzimidazol-5-yl | (R & S) cPent | Me | 54 | 0.34 (J) | | 409 (100%), 163 (40%) |
| XXXIII | 1-methyl-2-(allylthio)benzimidazol-5-yl | (R & S) cPent | Me | 61 | 0.39 (J) | | 420 (100%) |
| XXXIV | 1-methyl-2-(benzylthio)benzimidazol-5-yl | (R & S) cPent | Me | 68 | 0.54 (J) | | 471 (100%), 91 (55%) |
| XXXV | 1-methyl-2-(2,6-dichlorobenzylthio)benzimidazol-5-yl | (R & S) cPent | Me | 68 | 0.37 (D) 0.10 (O) | 60 (foam) | 541 (50%), 539 (80%), 163 (100%) |
| XXXVI | 1-methyl-2-(phenacylthio)benzimidazol-5-yl | (R & S) cPent | Me | 66 | 0.60 (J) | | 499 (100%) |
| XXXVII | 1-methyl-2-benzylbenzimidazol-5-yl | (R & S) cPent | tBu | 48 | 0.26 (E) | 136–27 | 481 (100%) |
| XXXVIII | 5,6-dichloro-1-methyl-2-benzylbenzimidazol-... | (R & S) cPent | tBu | 57 | 0.59 (J) | 154 | 57 (38%) |

TABLE IV-continued

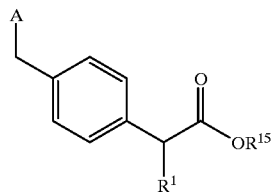

| Table No. | A | R¹ | R¹⁵ | Yield (% of theory) | R_f (solvent) | Melting point (°C.) | MS (relative intensity) |
|---|---|---|---|---|---|---|---|
| XXXIX | 5,6-diMe-1-Me-2-CF₃-benzimidazole | (R & S) cPent | tBu | 58 | 0.82 (K) | 132 | 549 (75%), 57 (100%) |
| XL | 1-Me-2-(thiazol-4-yl)-benzimidazole | (R & S) cPent | tBu | 62 | 0.22 (J) | 165 | 474 (100%) |
| XLI | 1-Me-2-(thiazol-4-yl)-benzimidazole | (R & S) cHex | Me | 97 | 0.23 (J) | 65 | 446 (100%), 163 (40%) |
| XLII | 1-Me-2-(thiazol-4-yl)-benzimidazole | (R & S) cHept | tBu | 86 | 0.24 (J) | 169 | *501 (100%), 57 (100%) |
| XLIII | 1-Me-2-(2-Me-thiazol-4-yl)-benzimidazole | (R & S) cPent | tBu | 70 | 0.31 (K) | 168–70 | 488 (100%) |
| XLIV | 1-Me-2-(2-Ph-thiazol-4-yl)-benzimidazole | (R & S) cPent | tBu | 62 | 0.48 (J) | 192 | 550 (100%) |
| XLV | 1-Me-2-(thien-3-yl)-benzimidazole | (R & S) cPent | tBu | 19 | 0.26 (J) | 164 | 473 (100%), 57 (35%) |
| XLVI | 5,6-diMe-1-Me-2-(thien-3-yl)-benzimidazole | (R & S) cPent | tBu | 51 | 0.41 (J) | 188 | 501 (100%) |

TABLE IV-continued

[Structure: A-CH2-C6H4-CH(R1)-C(=O)-OR15]

| Table No. | A | R1 | R15 | Yield (% of theory) | Rf (solvent) | Melting point (°C.) | MS (relative intensity) |
|---|---|---|---|---|---|---|---|
| XLVII | 1-methyl-2-(2-thienyl)benzimidazole | (R & S) cPent | tBu | 98 | 0.40 (E) | 154–59 | 473 (100%) |
| XLVIII | 4,5-dimethyl-1-methyl-2-(2-thienyl)benzimidazole | (R & S) cPent | tBu | 62 | 0.70 (J) | 186 | 501 (100%) |
| XLIX | 1-methyl-2-(benzothiophen-2-yl)benzimidazole | (R & S) cPent | tBu | 51 | 0.60 (E) 0.67 (J) | 188 | 523 (100%) |
| L | 1-methyl-2-(2-pyridyl)benzimidazole | (R & S) cPent | tBu | 68 | 0.45 (J) | 152 | 468 (100%) |
| LI | 1-methyl-2-(2-pyridyl)benzimidazole | (R & S) cHept | tBu | 91 | 0.28 (G) | 147 | *495 (100%), 57 (100%) |
| LII | 1-methyl-2-(3-pyridyl)benzimidazole | (R & S) cPent | tBu | 59 | 0.32 (K) | 107 | 468 (100%), 57 (40%) |
| LIII | 1-methyl-2-(4-pyridyl)benzimidazole | (R & S) cPent | tBu | 45 | 0.31 (K) | 98 | 468 (100%), 57 (50%) |
| LIV | 3-methyl-benzoxazol-2(3H)-one | (R & S) cHept | tBu | 65 | 0.41 (O) | 145 | *435 (100%), 57 (100%) |

TABLE IV-continued

[Structure: A-CH2-C6H4-CH(R1)-C(=O)-OR15]

| Table No. | A | R1 | R15 | Yield (% of theory) | Rf (solvent) | Melting point (°C.) | MS (relative intensity) |
|---|---|---|---|---|---|---|---|
| LV | 4-methyl-2-(methylthio)-1-methylbenzimidazol-yl | (R & S) cPent | tBu | 53 | 0.69 (J) | 78 | 451 (100%), 57 (70%) |
| LVI | 4-methyl-3-oxo-3,4-dihydro-2H-pyrido[3,2-b][1,4]oxazin-yl | (R & S) cHept | tBu | 100 | 0.31 (D) | 91 | 451 (70%), 395 (100%) |
| LVII | 4-methyl-3-oxo-3,4-dihydro-2H-pyrido[3,2-b][1,4]thiazin-yl | (R & S) cHept | tBu | 91 | 0.54 (D) | 133 | 465 (60%), 410 (100%) |
| LVIII | N-methylphthalimid-yl | (R & S) cHept | tBu | 76 | 0.53 (O) | 158 | 446 (50%), 57 (100%) |
| LIX | N-methyl-pyrido-phthalimid-yl | (R & S) cHept | tBu | 81 | 0.24 (J) | 133 | 449 (40%), 57 (100%) |
| LX | N-methylsaccharin-yl | (R & S) cHept | tBu | 70 | 0.48 (O) | 114 | |
| LXI | 3-methyl-2-ethyl-4-oxo-3,4-dihydroquinazolin-yl | (R & S) cPent | tBu | 29 | 0.46 (E) | oil | 447 (60%), 57 (100%) |

TABLE IV-continued

| Table No. | A | R¹ | R¹⁵ | Yield (% of theory) | $R_f$ (solvent) | Melting point (°C.) | MS (relative intensity) |
|---|---|---|---|---|---|---|---|
| LXII | (phthalazinone) | (R & S) cHept | tBu | 56 | 0.36 (E) | 151 | 447 (55%), 391 (100%) |
| LXIII | nBu-(phthalazinone) | (R & S) cPent | tBu | 74 | 0.84 (K) | oil | 475 (40%), 419 (100%) |
| LXIV | (4-Cl)—Ph-(phthalazinone) | (R & S) cPent | tBu | 93 | 0.90 (K) | oil | 529 (40%), 473 (100%) |

EXAMPLE LXV

Cyclopentyl-[4-(4-methyl-2-thioxo-2,3-dihydro-benzoimidazol-1-ylmethyl)phenyl]acetic acid

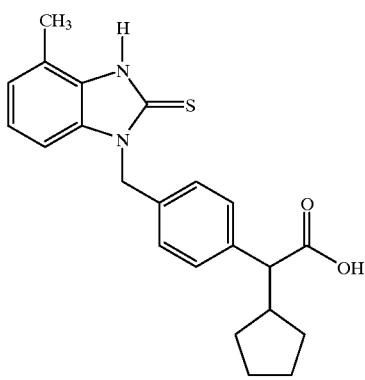

1.93 g (4.29 mmol) of the compound from Example LV are dissolved in 20 ml of dioxane, and 1 ml of concentrated hydrochloric acid is added to the solution. The mixture is boiled under reflux overnight and cooled, and 25 ml of cold water are added. The precipitate formed is filtered off with suction and dried.

Yield: 1.28 g (78.6%);
Melting point=>225° C.;
$R_f$=0.35 (CH$_2$Cl$_2$:methanol, 100:5);
Mass (calculated) for C$_{22}$H$_{24}$N$_2$O$_2$S=380.51

EXAMPLE LXVI

Cycloheptyl-[4-(2-thioxo-2,3-dihydro-benzoimidazol-1-ylmethyl)phenyl]acetic acid

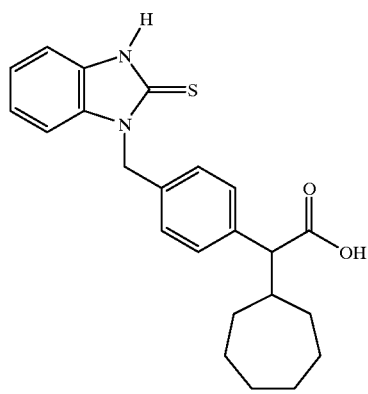

The reaction is carried out with 1.30 g of the compound from Example XXX analogously to the instructions of Example LXV.

Yield: 162 mg (15%);

Melting point=245° C.;

$R_f$=0.73 (petroleum ether:ethyl acetate, 2:1).

EXAMPLE LXVII

2-Cyclopentyl-2-[4-(2-methyl-4-oxo-4H-quinazolin-3-yl-methyl)phenyl]acetic acid

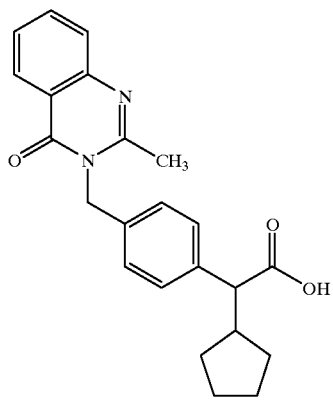

2.8 g (6.47 mmol) of the compound from Example XXXVII are dissolved in 25 ml of dioxane. 1.4 ml of concentrated hydrochloric acid are added and the mixture is boiled under reflux overnight. Water and $CH_2Cl_2$ are added and the mixture is extracted. The organic phase is dried over sodium sulphate and concentrated on a rotary evaporator. The residue is purified by column chromatography (silica gel Merck 60 (0.040–0.063)):

Yield: 1.68 g (68.9%);

Melting point=181° C. (foam);

$R_f$=0.39 ($CH_2Cl_2$:methanol 100:5);

Mass (calculated) for $C_{23}H_{24}N_2O_3$=376.459: mass spectrum (FAB, relative intensity) 378 (40%), 377 (100%);

$^1$H NMR (200 MHz, $CDCl_3$) δ8.31 (dd, J=7.74 Hz, J=1.06 Hz, 1 H), 7.80–7.62 (m, 2 H), 7.45 (m, 1 H), 7.29 (d, J=8.24 Hz, 2 H), 7.12 (d, J=8.17 Hz, 2 H), 5.36 (s, 2 H), 3.26 (d, J=11.12 Hz, 1 H), 2.51 (m, 1 H), 2.50 (s, 3 H), 1.95 (m, 1 H), 1.70–1.20 (m, 6 H), 0.97 (m, 1 H).

The compounds listed in Table V are prepared analogously to the instructions of Examples LXV–LXVII:

TABLE V

| Example No. | A | $R^1$ | Yield (% of theory) | $R_f$ (solvent) | Melting point (° C.) | MS (relative intensity) | Starting material (Example No.) |
|---|---|---|---|---|---|---|---|
| LXVIII | benzimidazole-S-Me (N-Me) | (R & S) cPent | 68 | 0.22 (K) | 198 | 381 (100%) | XXVII |
| LXIX | benzimidazole-S-Me (N-Me) | (R & S) cHept | 41 | 0.50 (J) | 229 | # 409 (100%) | XXVIII |
| LXX | 5,6-dimethylbenzimidazole-S-Me (N-Me) | (R & S) cPent | 64 | 0.19 (K) | 208 | 409 (100%), 154 (80%) | XXIX |
| LXXI | benzimidazole-S-Et (N-Me) | (R & S) cPent | 77 | 0.30 (K) | 180 | 395 (100%), 277 (60%) | XXX |

TABLE V-continued

| Example No. | A | R¹ | Yield (% of theory) | R_f (solvent) | Melting point (° C.) | MS (relative intensity) | Starting material (Example No.) |
|---|---|---|---|---|---|---|---|
| LXXII | 1-methyl-2-(allylthio)benzimidazol-2-yl | (R & S) cPent | 76 | 0.28 (K) | 159 | 407 (100%), 367 (45%) | |
| LXXIII | 1-methyl-2-(benzylthio)benzimidazol-2-yl | (R & S) cPent | 80 | 0.44 (K) | 165 | 457 (100%) | |
| LXXIV | 1-methyl-2-(2,6-dichlorobenzylthio)benzimidazol-2-yl | (R & S) cPent | 48 | 0.44 (K) | 104 (foam) | 527 (65%), 525 (100%) | |
| LXXV | 1-methyl-2-(phenacylthio)benzimidazol-2-yl | (R & S) cPent | 18 | 0.37 (K) | 96 (foam) | 485 (100%) | |
| LXXVI | 1-methyl-2-benzylbenzimidazol-2-yl (CH₂Ph) | (R & S) cPent | 58 | 0.35 (L) | 215–17 | 425 (100%) | |
| LXXVII | 5,6-dichloro-1-methyl-2-benzylbenzimidazol-2-yl (CH₂Ph) | (R & S) cPent | 100 | 0.33 (K) | >225 | 493 (100%), 307 (50%) | |
| LXXVIII | 5,6-dimethyl-1-methyl-2-(CF₃)benzimidazol-2-yl | (R & S) cPent | 36 | 0.33 (K) | 212 | 431 (100%) | |
| LXXIX | 1-methyl-2-(thiazol-4-yl)benzimidazol-2-yl | (R & S) cPent | 100 | 0.25 (K) | >210 | 419 (100%) | |

TABLE V-continued

| Example No. | A | R¹ | Yield (% of theory) | R_f (solvent) | Melting point (° C.) | MS (relative intensity) | Starting material (Example No.) |
|---|---|---|---|---|---|---|---|
| LXXX | benzimidazole-N-Me with thiazole | (R & S) cHex | 57 | 0.21 (K) | 232 | 432 (100%) | |
| LXXXI | benzimidazole-N-Me with thiazole | (R & S) cHept | 90 | 0.13 (K) 0.55 (L) | >204 | # 446 (100%) | |
| LXXXII | benzimidazole-N-Me with 2-Me-thiazole | (R & S) cPent | 72 | 0.33 (L) | >240 | 432 (100%), 154 (60%) | |
| LXXXIII | benzimidazole-N-Me with 2-Ph-thiazole | (R & S) cPent | 91 | 0.30 (K) | 163 | 494 (100%), 154 (60%) | XLII |
| LXXXIV | benzimidazole-N-Me with 3-thienyl | (R & S) cPent | 89 | 0.07 (K) 0.69 (L) | >220 | 417 (100%) | XLIII |
| LXXXV | 4,5-diMe-benzimidazole-N-Me with 3-thienyl | (R & S) cPent | 93 | 0.44 (K) | >238 | 445 (100%) | XLIL |
| LXXXVI | benzimidazole-N-Me with 2-thienyl | (R & S) cPent | 41 | 0.36 (L) | 223–25 | 417 (100%) | XLV |
| LXXXVII | 4,5-diMe-benzimidazole-N-Me with 2-thienyl | (R & S) cPent | 94 | 0.30 (K) | >210 | | XLVIII |

TABLE V-continued
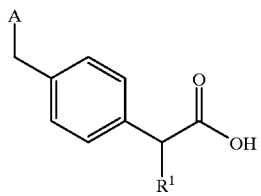
| Example No. | A | R[1] | Yield (% of theory) | $R_f$ (solvent) | Melting point (° C.) | MS (relative intensity) | Starting material (Example No.) |
|---|---|---|---|---|---|---|---|
| LXXXVIII | | (R & S) cPent | 85 | 0.27 (K) | 111–15 (foam) | 467 (100%), 154 (60%) | XLIX |
| LXXXIX | | (R & S) cPent | 67 | 0.57 (L) | >230 | *411 (100%), 342 (90%) | L |
| XC | | (R & S) cHept | 100 | 0.22 (K) | 118 (foam) | *439 (90%), 342 (100%) | LI |
| XCI | | (R & S) cPent | 64 | 0.59 (K) | 121 (foam) | 412 (100%) | LII |
| XCII | | (R & S) cPent | 94 | 0.37 (L) | 202 | 412 (100%), 307 (100%) | LIII |
| XCIII | | (R & S) cHept | 86 | 0.31 (K) 0.37 (H) | 212 | # 397 (100%), 334 (100%) | LIV |
| XCIV | | (R & S) cHept | 93 | 0.45 (K) | | *394 (30%), 57 (100%) | LVI |
| XCV | | (R & S) cHept | 69 | 0.44 (K) | 78 (foam) | *409 (50%), 165 (100%) | LVII |

TABLE V-continued

A-CH2-C6H4-CH(R1)-COOH

| Example No. | A | R1 | Yield (% of theory) | Rf (solvent) | Melting point (° C.) | MS (relative intensity) | Starting material (Example No.) |
|---|---|---|---|---|---|---|---|
| XCVI | N-methylphthalimide | (R & S) cHept | 88 | 0.36 (K) | 193 | *391 (20%), 295 (100%) | LVIII |
| XCVII | N-methyl pyrido-phthalimide | (R & S) cHept | 48 | 0.14 (K) | 107 (foam) | 393 (100%) | LIX |
| XCVIII | N-methyl benzisothiazolone-1,1-dioxide | (R & S) cHept | 90 | 0.38 (K) | 154 | | LX |
| XCIX | 2-ethyl-3-methyl-quinazolin-4(3H)-one | (R & S) cPent | 87 | 0.28 (K) | | 391 (100%) | LXI |
| C | 2-methylphthalazin-1(2H)-one | (R & S) cHept | 84 | 0.33 (K) | 176 | *390 (60%), 148 (100%) | LXII |
| CI | 4-nBu-2-methylphthalazin-1(2H)-one | (R & S) cPent | 100 | 0.30 (K) | | 419 (100%) | LXIII |
| CII | 4-(4-Cl-Ph)-2-methylphthalazin-1(2H)-one | (R & S) cPent | 69 | 0.30 (K) | 213–15 | 473 (40%), 353 (100%) | LXIV |

Preparation Examples

Example 1

2-Cyclopentyl-N-(2-hydroxy-1-(R)-phenylethyl)-2-[4-(2-methyl-4-oxo-4H-quinazolin-3-yl-methyl)phenyl]acetamide

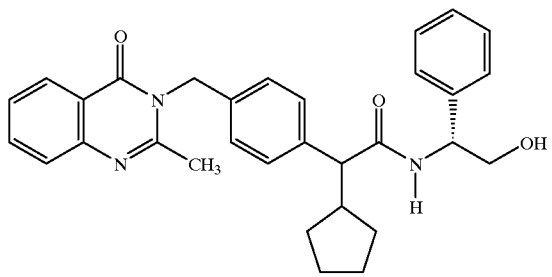

1.645 g (4.37 mmol) of the compound from Example LXVII are dissolved in 20 ml of $CH_2Cl_2$. 599 mg (4.37 mmol) of R-phenylglycinol, 649 mg (4.81 mmol) of 1-hydroxy-benzotriazole, 963 mg (5.02 mmol) of N'-(3-dimethylaminopropyl)-N-ethylcarbodiimide×HCl and 884 mg (8.74 mmol) of triethylamine are added in succession. The mixture is subsequently stirred overnight at room temperature. The solution is diluted with 20 ml of $CH_2Cl_2$ and extracted with saturated $NH_4Cl$ solution and saturated $NaHCO_3$ solution. The organic phase is dried over sodium sulphate and concentrated on a rotary evaporator. The residue is purified by column chromatography (silica gel Merck 60 (0.040–0.063):

Yield: 1.11 g (51.0%);

Melting point=97° C. (foam);

$R_f$=0.50 ($CH_2Cl_2$:methanol 100:5);

Mass (calculated) for $C_{31}H_{33}N_3O_3$=495.627; mass spectrum (FAB, relative intensity) 496 (100%), 307 (40%).

The compound listed in Table1 are prepared analogously to the instructions of Example 1:

TABLE 1

| Example No. | A | $R^1$ | Y | Yield (% of theory) | $R_f$ (solvent) | Melting point (° C.) | MS (relative intensity) | Starting material (Example No.) |
|---|---|---|---|---|---|---|---|---|
| 2 | benzimidazole-S-Me | cPent | (R & S) Ph-CH(NH)-CH2OH | 95 | 0.11 (K) | 83 (foam) | 500 (100%) | LXIX |
| 3 | benzimidazole-S-Me | cPent | (dia A) Ph-CH(NH)-CH2OH | | | 195–96 | | 2 |
| 4 | benzimidazole-S-Me | cPent | (dia B) Ph-CH(NH)-CH2OH | | | 215–16 | | 2 |
| 5 | benzimidazole-S-Me | cHept | (R & S) Ph-CH(NH)-CH2OH | 69 | 0.41 (K) | 175–77 | 528 (100%) | LXIX |
| 6 | benzimidazole-S-Me | cHept | (dia A) Ph-CH(NH)-CH2OH | | | 213 | | 5 |

TABLE 1-continued
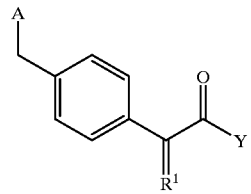
| Example No. | A | R¹ | Y | Yield (% of theory) | R_f (solvent) | Melting point (° C.) | MS (relative intensity) | Starting material (Example No.) |
|---|---|---|---|---|---|---|---|---|
| 7 | 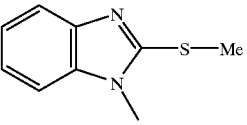 | (dia B) cHept | Ph, OH, NHMe | | | 188 | | 5 |
| 8 | 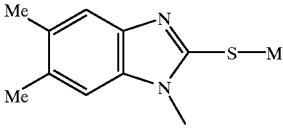 | (R & S) cPent | Ph, OH, NHMe | 74 | 0.17 (K) | 107 (foam) | 528 (100%) | LXX |
| 9 | 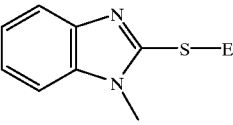 | (R & S) cPent | Ph, OH, NHMe | 60 | 0.39 (K) | 87 (foam) | 514 (100%) | LXXI |
| 10 | 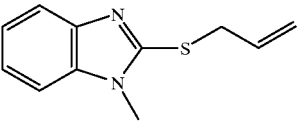 | (R & S) cPent | Ph, OH, NHMe | 69 | 0.40 (K) | 83 (foam) | 526 (100%) | LXXII |
| 11 | 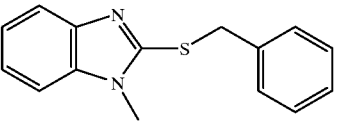 | (R & S) cPent | Ph, OH, NHMe | 52 | | 90 (foam) | 576 (100%) | LXXIII |
| 12 | 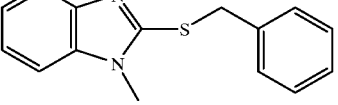 | (dia A) cPent | Ph, OH, NHMe | | 0.39 (K) | | | II |
| 13 | 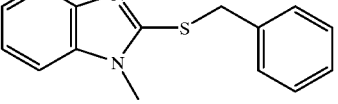 | (dia B) cPent | Ph, OH, NHMe | | 0.32 (K) | | | II |
| 14 | 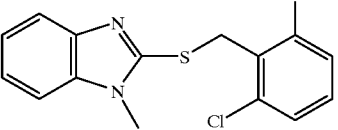 | (R & S) cPent | Ph, OH, NHMe | 85 | | | 644 (100%), 171 (50%) | LXXIV |

TABLE 1-continued

| Example No. | A | R¹ | Y | Yield (% of theory) | R_f (solvent) | Melting point (° C.) | MS (relative intensity) | Starting material (Example No.) |
|---|---|---|---|---|---|---|---|---|
| 15 | 1-methyl-2-[(2,6-dichlorobenzyl)thio]benzimidazole | (dia A) cPent | N-Me, CH(Ph)CH2OH | | 0.44 (K) | 217 | | 14 |
| 16 | 1-methyl-2-[(2,6-dichlorobenzyl)thio]benzimidazole | (dia B) cPent | N-Me, CH(Ph)CH2OH | | 0.35 (K) | 115 | | 14 |
| 17 | 1-methyl-2-(phenacylthio)benzimidazole | (R & S) cPent | N-Me, CH(Ph)CH2OH | 39 | | 90 | 604 (100%) | LXXV |
| 18 | 1-methyl-2-(phenacylthio)benzimidazole | (dia A) cPent | N-Me, CH(Ph)CH2OH | | 0.44 (K) | | | 17 |
| 19 | 1-methyl-2-(phenacylthio)benzimidazole | (dia B) cPent | N-Me, CH(Ph)CH2OH | | 0.35 (K) | | | 17 |
| 20 | 1-methyl-2-(phenacylthio)benzimidazole | (R & S) cPent | N-Me, CH(Ph)CH2OH | 64 | 0.39 (K) | (foam) | 544 (100%) | LXXVI |
| 21 | 5,6-dichloro-1-methyl-2-benzylbenzimidazole | (R & S) cPent | N-Me, CH(Ph)CH2OH | 91 | 0.40 (K) | 98 (foam) | 614 (75%), 612 (100%) | LXXVII |
| 22 | 5,6-dimethyl-1-methyl-2-(trifluoromethyl)benzimidazole | (R & S) cPent | N-Me, CH(Ph)CH2OH | 85 | 0.28 (K) | 92 (foam) | 550 (100%), 105 (65%) | LXXVIII |

TABLE 1-continued

| Example No. | A | R¹ | Y | Yield (% of theory) | $R_f$ (solvent) | Melting point (° C.) | MS (relative intensity) | Starting material (Example No.) |
|---|---|---|---|---|---|---|---|---|
| 23 | 5,6-diMe-1-Me-2-CF₃-benzimidazole | (dia A) cPent | N-Me, CH(Ph)-CH₂OH | | | 178 | | 22 |
| 24 | 5,6-diMe-1-Me-2-CF₃-benzimidazole | (dia B) cPent | N-Me, CH(Ph)-CH₂OH | | | 204 | | 22 |
| 25 | 1-Me-2-(thiazol-4-yl)-benzimidazole | (R & S) cPent | N-Me, CH(Ph)-CH₂OH | 62 | 0.28 (K) | 104 (foam) | 537 (100%) | LXXIX |
| 26 | 1-Me-2-(thiazol-4-yl)-benzimidazole | (dia A) cPent | N-Me, CH(Ph)-CH₂OH | | | 208–09 | | 25 |
| 27 | 1-Me-2-(thiazol-4-yl)-benzimidazole | (dia B) cPent | N-Me, CH(Ph)-CH₂OH | | | 199–201 | | 25 |
| 28 | 1-Me-2-(thiazol-4-yl)-benzimidazole | (R & S) cHex | N-Me, CH(Ph)-CH₂OH | 81 | 0.38 (K) | 122 (foam) | 551 (100%), 154 (40%) | LXXX |
| 29 | 1-Me-2-(thiazol-4-yl)-benzimidazole | (R & S) cHept | N-Me, CH(Ph)-CH₂OH | 77 | 0.27 (K) | 213 | 565 (100%) | LXXXI |
| 30 | 1-Me-2-(thiazol-4-yl)-benzimidazole | (dia A) cHept | N-Me, CH(Ph)-CH₂OH | | | >230 | | 29 |

TABLE 1-continued

| Example No. | A | R¹ | Y | Yield (% of theory) | R_f (solvent) | Melting point (° C.) | MS (relative intensity) | Starting material (Example No.) |
|---|---|---|---|---|---|---|---|---|
| 31 | 1-methyl-2-(thiazol-4-yl)benzimidazole | (dia B) cHept | NHMe-CH(Ph)-CH2OH | | | 177 | | 29 |
| 32 | 1-methyl-2-(thiazol-4-yl)benzimidazole | (R & S) cHept | NH-CH2-Ph | 75 | 0.37 (K) | 182 | 535 (100%) | LXXXI |
| 33 | 1-methyl-2-(2-methylthiazol-4-yl)benzimidazole | (R & S) cPent | NHMe-CH(Ph)-CH2OH | 78 | 0.18 (K) | 104 (foam) | 551 (100%) | LXXXII |
| 34 | 1-methyl-2-(2-methylthiazol-4-yl)benzimidazole | (dia A) cPent | NHMe-CH(Ph)-CH2OH | | | 108 (foam) | | 33 |
| 35 | 1-methyl-2-(2-methylthiazol-4-yl)benzimidazole | (dia B) cPent | NHMe-CH(Ph)-CH2OH | | | 108 (foam) | | 33 |
| 36 | 1-methyl-2-(2-phenylthiazol-4-yl)benzimidazole | (R & S) cPent | NHMe-CH(Ph)-CH2OH | 63 | 0.33 (K) | 227 | 613 (100%). 154 (75%) | LXXXIII |
| 37 | 1-methyl-2-(thien-3-yl)benzimidazole | (R & S) cPent | NHMe-CH(Ph)-CH2OH | 83 | 0.50 (L) | 103 (foam) | 535 (100%), 307 (42%) | LXXXIV |
| 38 | 1,4,5-trimethyl-2-(thien-3-yl)benzimidazole | (R & S) cPent | NHMe-CH(Ph)-CH2OH | 57 | 0.44 (K) | 131 | 564 (100%) | LXXXV |

TABLE 1-continued

Structure: 4-substituted phenyl group with CH₂-A at para position and -C(=R¹)-C(=O)-Y at the other position.

| Example No. | A | R¹ | Y | Yield (% of theory) | R_f (solvent) | Melting point (° C.) | MS (relative intensity) | Starting material (Example No.) |
|---|---|---|---|---|---|---|---|---|
| 39 | 2-(thiophen-2-yl)-1-methylbenzimidazole | (R & S) cPent | N-Me, (S)-PhCH(NHMe)CH₂OH | 61 | 0.43 (K) | (foam) | 536 (100%) | LXXXVI |
| 40 | 4,5-dimethyl-2-(thiophen-2-yl)-1-methylbenzimidazole | (R & S) cPent | (S)-PhCH(NHMe)CH₂OH | 52 | 0.30 (K) | 110 | 564 (100%) | LXXXVII |
| 41 | 2-(benzothiophen-2-yl)-1-methylbenzimidazole | (R & S) cPent | (S)-PhCH(NHMe)CH₂OH | 59 | | 120–22 (foam) | 586 (100%) | LXXXVIII |
| 42 | 2-(benzothiophen-2-yl)-1-methylbenzimidazole | (dia A) cHept | (S)-PhCH(NHMe)CH₂OH | | 0.35 (K) | | | 41 |
| 43 | 2-(benzothiophen-2-yl)-1-methylbenzimidazole | (dia B) cHept | (S)-PhCH(NHMe)CH₂OH | | 0.31 (K) | | | 41 |
| 44 | 2-(pyridin-2-yl)-1-methylbenzimidazole | (R & S) cPent | (S)-PhCH(NHMe)CH₂OH | 97 | 0.43 (K) | 103 (foam) | 531 (100%) | LXXXIX |
| 45 | 2-(pyridin-2-yl)-1-methylbenzimidazole | (R & S) cHept | (S)-PhCH(NHMe)CH₂OH | 77 | 0.34 (K) | 107 (foam) | # 559 (100%) | XC |

TABLE 1-continued

[Structure: A-CH2-C6H4-C(=R1)-C(=O)-Y]

| Example No. | A | R¹ | Y | Yield (% of theory) | R_f (solvent) | Melting point (° C.) | MS (relative intensity) | Starting material (Example No.) |
|---|---|---|---|---|---|---|---|---|
| 46 | 1-methyl-2-(2-pyridyl)benzimidazole | (dia A) cHept | N-methyl, CH(Ph)CH2OH | | | >225 | | 45 |
| 47 | 1-methyl-2-(2-pyridyl)benzimidazole | (dia B) cHept | N-methyl, CH(Ph)CH2OH | | | 188 | | 45 |
| 48 | 1-methyl-2-(2-pyridyl)benzimidazole | (R & S) cHept | N-benzyl | 64 | 0.36 (K) | 177 | 529 (100%) | XC |
| 49 | 1-methyl-2-(3-pyridyl)benzimidazole | (R & S) cPent | N-methyl, CH(Ph)CH2OH | 85 | 0.45 (L) | 104 (foam) | 531 (70%) 154 (100%) | XCI |
| 50 | 1-methyl-2-(4-pyridyl)benzimidazole | (R & S) cPent | N-methyl, CH(Ph)CH2OH | 79 | 0.47 (L) | 109 (foam) | 531 (100%) 307 (100%) | XCII |
| 51 | 3-methyl-benzoxazol-2(3H)-one | (R & S) cHept | N-methyl, CH(Ph)CH2OH | 75 | 0.45 (K) | 161 (foam) | 499 (100%) | XCIII |
| 52 | 1-methyl-benzimidazole-2-thione | (R & S) cHept | N-methyl, CH(Ph)CH2OH | 76 | 0.31 (K) | 136 (foam) | 514 (100%) | LXV |
| 53 | 4-methyl-1-methyl-benzimidazole-2-thione | (R & S) cPent | N-methyl, CH(Ph)CH2OH | 32 | 0.31 (K) | | 500 (100%), 307 (40%) | LXIV |

TABLE 1-continued
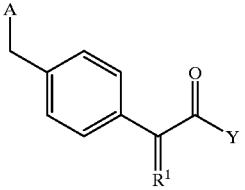
| Example No. | A | R¹ | Y | Yield (% of theory) | R_f (solvent) | Melting point (° C.) | MS (relative intensity) | Starting material (Example No.) |
|---|---|---|---|---|---|---|---|---|
| 54 | 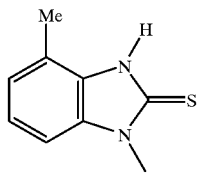 | (dia A) cPent | 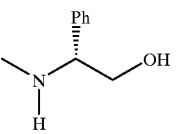 | | | 240 | | 53 |
| 55 | 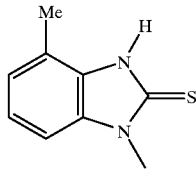 | (dia B) cPent | 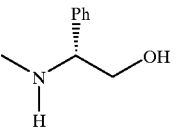 | | | 257 | | 53 |
| 56 | 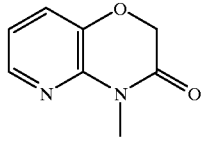 | (R & S) cHept | 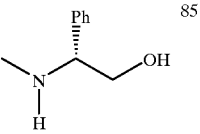 | 85 | 0.33 (K) | 110 | 514 (100%) | XCIV |
| 57 | 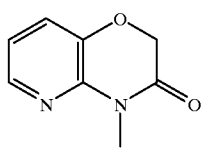 | (dia A) cHept | 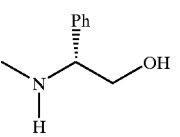 | | | 92 | | 56 |
| 58 | 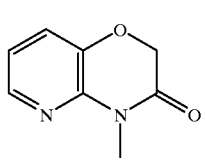 | (dia B) cHept | 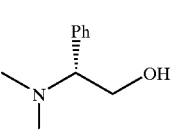 | | | 175 | | 56 |
| 59 | 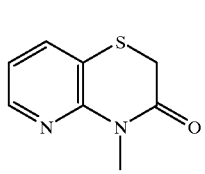 | (R & S) cHept | 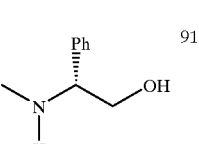 | 91 | 0.31 (K) | 151 | 529 (100%) | XCV |
| 60 | 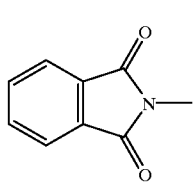 | (R & S) c Hept | 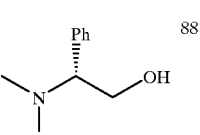 | 88 | | 143 | 511 (60%), 77 (100%) | XCVI |

TABLE 1-continued
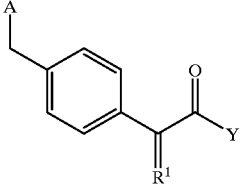
| Example No. | A | R¹ | Y | Yield (% of theory) | R_f (solvent) | Melting point (° C.) | MS (relative intensity) | Starting material (Example No.) |
|---|---|---|---|---|---|---|---|---|
| 61 | 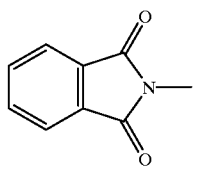 | (dia A) cHept | 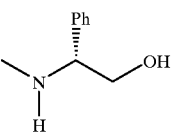 | | 0.43 (K) | | | 60 |
| 62 | 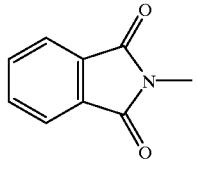 | (dia B) cHept | 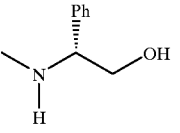 | | 0.26 (K) | | | 60 |
| 63 | 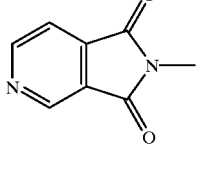 | (R & S) cHept | 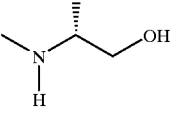 | 68 | 0.39 (K) | 97 (foam) | 512 (100%) | XCVII |
| 64 | 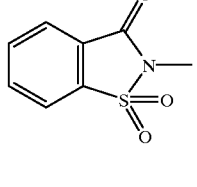 | (R & S) cHept | 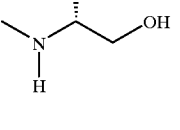 | 48 | 0.46 (K) | 157 | 547 (100%), 199 (100%) | XCVIII |
| 65 | 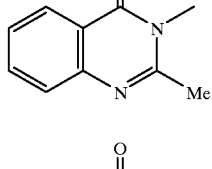 | (dia A) cPent | 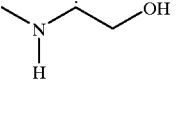 | | | 208 | | 1 |
| 66 | 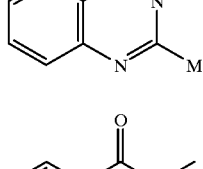 | (dia B) cPent | 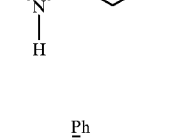 | | | 228 | | 1 |
| 67 | 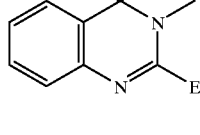 | (R & S) cPent | 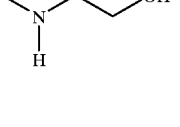 | 46 | 0.31 (K) | | #527 (M + NH₄, 80%), 510 (100%) | XCIX |

TABLE 1-continued
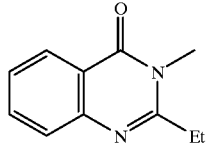
| Example No. | A | R¹ | Y | Yield (% of theory) | $R_f$ (solvent) | Melting point (° C.) | MS (relative intensity) | Starting material (Example No.) |
|---|---|---|---|---|---|---|---|---|
| 68 | 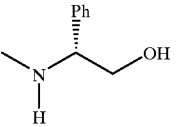 | (dia A) cPent | 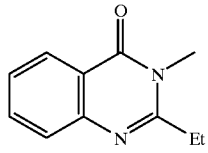 | | | 177–79 | | 67 |
| 69 | 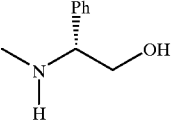 | (dia B) cPent | 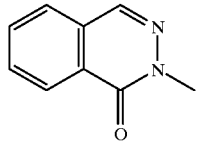 | | | 180–183 | | 67 |
| 70 | 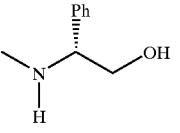 | (R & S) cHept | 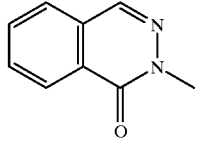 | 90 | | 96 (foam) | 510 (100%) | C |
| 71 | 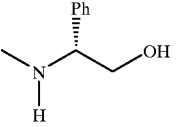 | (dia A) cPent | 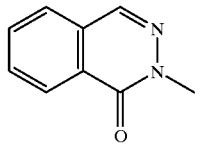 | | 0.33 (K) | | | 70 |
| 72 | 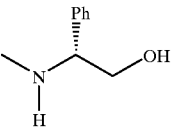 | (dia B) cPent | 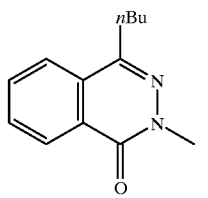 | | 0.30 (K) | | | 70 |
| 73 | 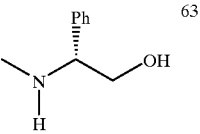 | (R & S) cPent | | 63 | 0.25 (H) | | 538 (100%) | CI |

TABLE 1-continued
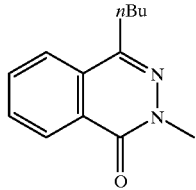
| Example No. | A | R¹ | Y | Yield (% of theory) | R_f (solvent) | Melting point (° C.) | MS (relative intensity) | Starting material (Example No.) |
|---|---|---|---|---|---|---|---|---|
| 74 | 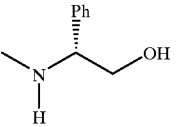 | (dia A) cPent | 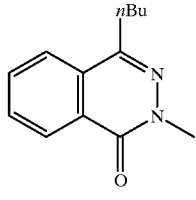 | | | (foam) | | 73 |
| 75 | 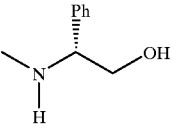 | (dia B) cPent | 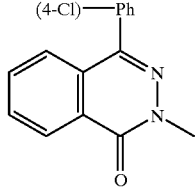 | | | 161–64 | | 73 |
| 76 | 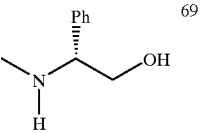 | (R & S) cPent | 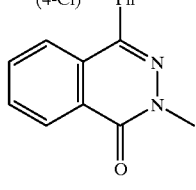 | 69 | 0.33 (K) | | 592 (100%) | CII |
| 77 | 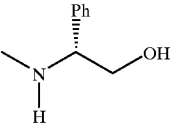 | (dia A) cPent | 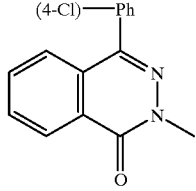 | | | (foam) | | 76 |
| 78 | 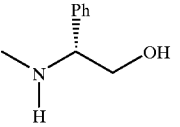 | (dia B) cPent | | | | (foam) | | 76 |

Example 79

2-(R/S)-Cycloheptyl-N-(2-hydroxy-1-(R)-phenylethyl)-2-[4-(2-methyl-(R/S)-sulphinyl-benzimidazol-1-ylmethyl)phenyl]acetamide

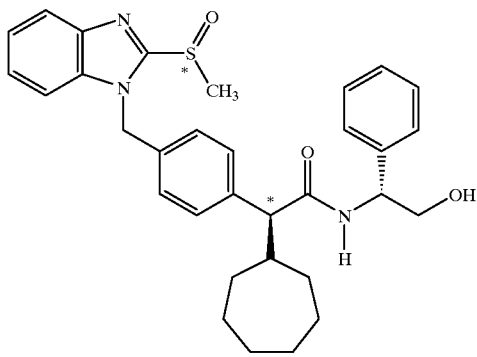

0.30 g (0.568 mmol) of the compound from Example 6 is dissolved in 10 ml of $CH_2Cl_2$ and the solution is cooled to 0° C. 0.178 g (5.68 mmol, 55% pure) of m-chloroperbenzoic acid is slowly added. The mixture is subsequently stirred at 0° C. for 30 minutes and then at room temperature. After 1 hour, a little $CH_2Cl_2$ and saturated $NaHCO_3$ solution are added and the mixture is extracted. The organic phase is dried over sodium sulphate, concentrated on a rotary evaporator and purified by column chromatography. (Silica gel Merck 60 (0.040–0.063)):

Yield: 33 mg (10.7%);
Melting point=158° C.;
$R_f$=0.25 ($CH_2Cl_2$:methanol 100:5);
Mass (calculated) for $C_{32}H_{37}N_3O_3S$=543.74;
Mass spectrum (FAB, relative intensity) 444 (25%), 154 (80%), 55 (100%).

What is claimed is:
1. A bicyclic heterocyclic compound of the formula (I):

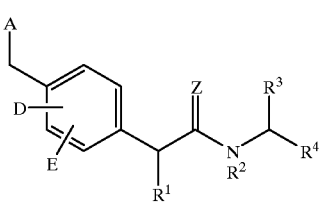

(I)

in which
A represents a radical of the formula

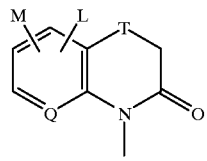

wherein
L and M are identical or different and denote hydrogen, halogen, trifluoromethyl, carboxyl, cycloalkyl having 3 to 6 carbon atoms, hydroxyl, phenyl or straight-chain or branched alkyl, alkoxycarbonyl or alkoxy having in each case up to 6 carbon atoms, Q denotes a nitrogen atom or the —CH group,
T denotes a group of the formula —$SO_2$ or —CO or an oxygen or sulphur atom,
D and E are identical or different and represent hydrogen, halogen, trifluoromethyl, hydroxyl or carboxyl, or represent straight-chain or branched alkyl, alkoxy or alkoxycarbonyl having in each case up to 6 carbon atoms,
Z represents an oxygen or sulphur atom,
$R^1$ represents cycloalky having 3 to 10 carbon atoms, or represents straight-chain or branched alkyl having 1 to 10 carbon atoms, or represents phenyl, which is optionally substituted up to twice in an identical or different manner by halogen, nitro, cyano, hydroxyl or straight-chain or branched alkyl or alkoxy having in each case up to 4 carbon atoms,
$R^2$ represents hydrogen or straight-chain or branched alkyl having up to 3 carbon atoms,
$R^3$ represents hydrogen or straight-chain or branched alkyl having up to 5 carbon atoms, or represents cycloalkyl having 3 to 7 carbon atoms, or represents phenyl, or represents a 5- to 7- membered aromatic heterocyclic radical having up to 3 hetroatoms independently selected from the group consisting of S, N and O, which are optionally substituted up to 3 times in an identical or different manner by halogen, nitro, phenyl, or hydroxyl or by straight-chain or branched alkyl or alkoxy having up to 6 carbon atoms,
$R^4$ represents hydrogen, or represents a group of the formula —$CH_2$—OH or —$CH_2O$—CO—$R^{11}$, wherein
$R^{11}$ denotes hydrogen, straight-chain or branched alkyl having up to 8 carbon atoms or phenyl, which is optionally substituted up to 3 times in an identical or different manner by halogen, hydroxyl, cyano or straight-chain or branched alkyl or alkoxy having in each case up to 4 carbon atoms, or a salt thereof.

2. A bicyclic heterocyclic compound of the formula (I) according to claim 1, in which
A represents a radical of the formula

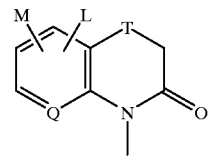

wherein
L and M are identical or different and denote hydrogen, fluorine, chlorine, bromine, trifluoromethyl, cyclopropyl, cyclobutyl, cyclopentyl, cyclohexyl, hydroxyl, phenyl or straight-chain or branched alkyl, alkoxycarbonyl or alkoxy having in each case up to 5 carbon atoms,
Q denotes a nitrogen atom or the —CH group,
T denotes a group of the formula —$SO_2$ or —CO or an oxygen or sulphur atom,
D and E are identical or different and represent hydrogen, fluorine, chlorine, bromine, trifluoromethyl, hydroxyl or straight-chain or branched alkyl or alkoxy having in each case up to 4 carbon atoms,
Z represents an oxygen or sulphur atom,
$R^1$ represents cyclobutyl, cyclopentyl, cyclohexyl, cycloheptyl or cyclooctyl, or represents straight-chain or branched alkyl having up to 7 carbon atoms, or represents phenyl, which is optionally substituted by fluorine, chlorine, bromine, nitro, cyano, hydroxyl or straight-chain or branched alkyl or alkoxy having in each case up to 3 carbon atoms, $R^2$ denotes hydrogen or methyl, $R^3$ represents hydrogen or straight-chain or branched alkyl having up to 4 carbon atoms, benzyl, cyclopropyl, cyclopentyl or cyclohexyl, or represents phenyl, pyridyl, thienyl or furyl, which are optionally substituted up to twice in an identical or different manner by fluorine, chlorine, bromine, phenyl, nitro, or hydroxyl or by straight-chain or branched alkyl or alkoxy having up to 4 carbon atoms, $R^4$ represents hydrogen, or represents a group of the formula —$CH_2$—OH or —$CH_2O$—CO—$R^{11}$, wherein $R^{11}$ denotes hydrogen, straight-chain or branched alkyl having up to 6 carbon atoms or phenyl, which is optionally substituted up to twice in an identical or different manner by fluorine, chlorine, bromine, cyano, hydroxyl or straight-chain branched alkyl or alkoxy having in each case up to 3 carbon atoms, or a salt thereof.

3. A bicyclic heterocyclic compound of the formula according to claim 1, in which A represents a radical of the formula

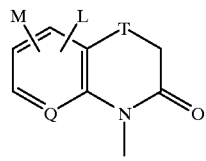

wherein

L and M are identical or different and denote hydrogen, fluorine, chlorine, bromine, hydroxyl, phenyl or straight-chain or branched alkyl or alkoxy having in each case up to 4 carbon atoms, Q denotes a nitrogen atom or the —CH group, T denotes a group of the formula —$SO_2$ or —CO or an oxygen or sulphur atom, D and E are identical or different and represent hydrogen, fluorine, chlorine, bromine or trifluoromethyl, Z represents oxygen, $R^1$ represents cyclopentyl, cyclohexyl, cycloheptyl or cyclooctyl, or represents straight-chain or branched alkyl having up to 6 carbon atoms, $R^2$ represents hydrogen or methyl, $R^3$ represents phenyl and $R^4$ represents the group —$CH_2$—OH, or a salt thereof.

4. A composition for the treatment of atherosclerosis comprising an amount effective therefor of a compound or salt thereof according to claim 1 and a pharmacologically acceptable diluent.

5. The method of treating atherosclerosis in a patient in need thereof which comprises administering to such patient an amount effective therefor of a compound or salt thereof according to claim 1.

* * * * *